US010632184B2

(12) United States Patent
Livengood et al.

(10) Patent No.: US 10,632,184 B2
(45) Date of Patent: Apr. 28, 2020

(54) COMPOSITIONS AND METHODS FOR STABILIZING ALPHAVIRUSES WITH IMPROVED FORMULATIONS

(71) Applicant: Takeda Vaccines, Inc., Cambridge, MA (US)

(72) Inventors: Jill Ann Livengood, Fort Collins, CO (US); Timothy Duane Powell, Maynard, MA (US)

(73) Assignee: TAKEDA VACCINES, INC., Cambridge, MA (US)

( * ) Notice: Subject to any disclaimer, the term of this patent is extended or adjusted under 35 U.S.C. 154(b) by 0 days.

(21) Appl. No.: 16/088,816

(22) PCT Filed: Mar. 27, 2017

(86) PCT No.: PCT/US2017/024365
§ 371 (c)(1),
(2) Date: Sep. 26, 2018

(87) PCT Pub. No.: WO2017/172643
PCT Pub. Date: Oct. 5, 2017

(65) Prior Publication Data

US 2019/0111124 A1 Apr. 18, 2019

Related U.S. Application Data

(60) Provisional application No. 62/316,262, filed on Mar. 31, 2016.

(51) Int. Cl.

| | |
|---|---|
| ***A61K 47/26*** | (2006.01) |
| ***A61K 39/12*** | (2006.01) |
| ***A61K 9/19*** | (2006.01) |
| ***A61K 47/18*** | (2017.01) |
| ***A61K 9/00*** | (2006.01) |
| *A61K 39/00* | (2006.01) |

(52) U.S. Cl.
CPC ............ *A61K 39/12* (2013.01); *A61K 9/0019* (2013.01); *A61K 9/19* (2013.01); *A61K 47/183* (2013.01); *A61K 47/26* (2013.01); *A61K 2039/5254* (2013.01); *C12N 2770/36134* (2013.01)

(58) Field of Classification Search
CPC .................... A61K 39/00; A61K 48/00; A61K 2039/5254; A61K 39/12; A61K 47/183; A61K 47/26; C07K 14/005; C12N 15/79; C12N 15/86
See application file for complete search history.

(56) References Cited

U.S. PATENT DOCUMENTS 5,545,555 A 8/1996 Racioppi

FOREIGN PATENT DOCUMENTS

WO 2008026225 A2 3/2008
WO 2014151855 A1 9/2014

OTHER PUBLICATIONS

Michael Onken in MedSci Network: Biochemistry: Rec: Why is histidine able to act as a buffer as pH.6.0, published on Pril. 15, 12: 01:17, 2002, ID 1018796921.Bc.*
Burke, C., et al. "Formulation, Stability, and Delivery of Live Attenuated Vaccines for Human Use". Critical Reviews in Therapeutic Drug Carrier Sys, Begell House Publishing Inc., vol. 16, No. 1, pp. 1-83, 1999.
International Search Report and Written Opinion for PCT/US2017/024365 dated Oct. 5, 2017, 9 pages.

* cited by examiner

*Primary Examiner* — Bao Q Li
(74) *Attorney, Agent, or Firm* — Honigman LLP; Fernando Alberdi; Jonathan P. O'Brien

(57) ABSTRACT

Embodiments herein relate to compositions and methods for stabilizing live alphaviruses. Other embodiments relate to compositions and methods for reducing degradation of live, attenuated alphaviruses. Certain embodiments relate to providing a stabilizing composition while reducing immune reaction in a subject to excipients that stabilize the live alphaviruses by providing improved formulations. Yet other embodiments relate to uses of compositions disclosed herein in kits for portable applications and methods wherein the compositions reduce degradation of the live alphaviruses.

62 Claims, 20 Drawing Sheets

| | Rx1 | Rx2 | Rx3 | Rx4 | Rx5 | Rx6 | Rx7 | Rx8 |
|---|---|---|---|---|---|---|---|---|
| 4C, 26W | 0.18 | -0.56 | -1.53 | -1.20 | -1.71 | -0.37 | -0.61 | -1.94 |
| 25C, 12W | -0.22 | -1.58 | -2.40 | -3.14 | -5.30 | -1.13 | -1.11 | -2.52 |
| 40C, 4W | -1.06 | -2.37 | -4.20 | -5.30 | -5.30 | -2.62 | -1.65 | -5.30 |

| | Rx1 | Rx2 | Rx3 | Rx4 | Rx5 | Rx6 | Rx7 | Rx8 | Rx9 | Rx10 | Rx11 | Rx12 | Rx13 | Rx14 | Rx15 | Rx16 | Rx17 |
|---|---|---|---|---|---|---|---|---|---|---|---|---|---|---|---|---|---|
| 4C, 12W | -1.2 | -1.2 | -1.1 | -1.5 | -1.4 | -1.2 | -1.3 | -1.1 | -1.4 | -1.3 | -1.9 | -1.6 | -1.7 | -1.3 | -1.1 | -1.4 | -0.0 |
| 25C, 12W | -1.6 | -1.9 | -1.3 | -1.9 | -2.1 | -1.9 | -1.8 | -1.8 | -1.8 | -1.8 | -2.5 | -2.4 | -2.5 | -2.2 | -1.7 | -2.1 | -1.1 |
| 40C, 6W | -3.3 | -5.3 | -3.1 | -4.2 | -5.3 | -3.5 | -5.3 | -3.4 | -3.3 | -3.4 | -5.3 | -5.3 | -5.3 | -5.3 | -3.8 | -3.7 | -1.9 |

| | 1 | 2 | 3 | 4 | 5 | 6 | 7 | 8 | 9 | 10 |
|---|---|---|---|---|---|---|---|---|---|---|
| 4C week 12 (53d) | -0.59 | -0.61 | -0.65 | -0.68 | -0.37 | -0.55 | -0.72 | -0.27 | -0.85 | -0.60 |
| 25C week 12 | -1.26 | -1.40 | -1.78 | -1.57 | -1.07 | -1.51 | -2.11 | -1.28 | -1.59 | -0.98 |
| 40C Week 6 | -2.19 | -2.85 | -2.50 | -2.28 | -2.05 | -2.71 | -2.75 | -2.06 | -2.03 | -2.40 |

COMPOSITIONS AND METHODS FOR STABILIZING ALPHAVIRUSES WITH IMPROVED FORMULATIONS

CROSS-REFERENCE TO RELATED APPLICATIONS

This application claims priority under 35 U.S.C. § 371 to Patent Cooperation Treaty Application PCT/US2017/024365, filed Mar. 27, 2017, which claims the benefit under 35 USC § 119(e) of provisional U.S. patent application Ser. No. 62/316,262 filed on Mar. 31, 2016, the entire contents of both of which are incorporated herein by reference in their entireties.

GOVERNMENT FUNDING

This invention was made with Government support under grant R01AI093491 awarded by the National Institutes of Health. The Government has certain rights in this invention.

FIELD

Embodiments herein relate to compositions and methods for stabilizing alphaviruses. In certain embodiments, compositions and methods disclosed herein concern stabilizing live alphaviruses or stabilizing live, attenuated alphaviruses. Other embodiments relate to compositions and methods for reducing degradation of alphaviruses. Yet other embodiments relate to providing formulations for live, attenuated or live alphaviruses with reduced immune reaction in a subject to excipients for the live, attenuated or live alphaviruses by providing improved formulations for stabilization and delivery of a composition disclosed herein to a subject. Other embodiments relate to formulations directed to mannitol, histidine and sucrose in a HEPES buffer having no human or other mammalian-derived byproducts such as proteins. Yet other embodiments relate to alphavirus formulations of use in kits for portable applications and methods.

BACKGROUND

Vaccines to protect against viral infections have been used effectively to reduce incidence of human or animal viral diseases. One of the most successful technologies for viral vaccines is to immunize animals or humans with a weakened or attenuated strain of the target virus (a "live, attenuated virus"). Due to limited replication after immunization of a subject, an attenuated strain does not cause viral-related diseases because it can't be duplicated and passed onto a host. However, the attenuated virus is still capable of expressing viral antigens and can generate potent and long-lasting immune responses to the virus in the exposed subject. Therefore, upon subsequent exposure to the virus, the immunized individual has a reduced chance of developing diseases related to viral infection.

In order for live, attenuated viruses to be effective in a vaccine, the live, attenuated viruses must be capable of replicating after immunization and the viruses themselves must be protected from degradation in order to be used effectively and accurately. Some vaccines are sensitive to temperature extremes; either excessive heat or accidental freezing can inactivate the viruses. Maintaining an effective and protective environment throughout distribution is particularly difficult in developing countries or when treating patients in remote areas.

SUMMARY

Embodiments herein relate to compositions and methods for stabilizing live, alphaviruses. Other embodiments relate to compositions and methods for reducing degradation and/or stabilizing live, attenuated alphaviruses of use in immunogenic compositions for immunizing a subject against infection caused by the alphavirus. Other embodiments relate to providing stabilizing compositions that do not contain human or other mammalian byproducts in order to reduce immune reaction in a subject to excipients that stabilize the live, attenuated alphaviruses. In accordance with these embodiments, stabilizing formulations do not contain animal byproducts when used as an immunogenic composition against alphavirus infections in a subject. Yet other embodiments relate to use of stabilizing compositions disclosed herein in kits for portable applications and methods.

In some embodiments, certain compositions disclosed herein can include combinations of components that reduce degradation of a live, attenuated alphaviruses while providing a formulation having reduced allergic reactions by a subject when administered to the subject. Certain formulations disclosed herein were designed to provide a higher level of safety of immunogenic alphavirus formulations by considering purity of raw materials used to stabilize alphaviruses of use in the immunogenic alphavirus formulations. Some formulations of the past use animal-derived excipients for stabilizing viruses and other agents. In certain situations, some of these animal-derived excipients and proteins can carry extraneous agents (e.g. BSE or allergens) which can cause adverse reactions in a subject when exposed to these agents. Formulation free of human or other mammalian-derived excipients reduces risk of introducing an unknown or unsafe agent to the subject (e.g. impurities associated with these agents). Animal-derived agent-free formulations that stabilize as well as, or better than, animal-derived agent-containing formulations are provided herein. Other embodiments disclosed herein concern combinations of excipients that greatly enhance stability of live, attenuated alphaviruses. Yet embodiments are directed to other compositions and methods for enhancing stability of virus formulations at all temperature ranges of storage and for reducing the need for lower temperatures (e.g. refrigerated or frozen storage) in order to facilitate stabilized transfer of virus formulations to remote areas. In other embodiments, compositions and methods disclosed herein concern reducing resuspension time of a composition, and/or improving physiological properties as well as increasing shelf-life of aqueous and/or reconstituted live alphaviruses compared to other formulations not containing these compositions.

In certain embodiments, formulations disclosed herein are capable of conferring stabilizing effects from loss of virus titer in liquid, frozen, lyophilized and rehydrated formulation. In other embodiments, compositions disclosed herein concern live alphaviruses or live, attenuated alphavirus compositions including, but not limited to, one or more live alphavirus, HEPES buffer, one or more amino acids, and one or more carbohydrate agents. In other embodiments, a stabilizing compositions disclosed herein can include live alphaviruses in a HEPES buffer, an amino acid that includes histidine, and one or more carbohydrate agents that includes one or more of sucrose and mannitol. In yet other embodiments, live alphavirus formulations can include live, alphaviruses, in a HEPES based buffer with histidine, mannitol and sucrose.

In some embodiments, alphavirus formulations, can include, but are not limited to, one or more live, attenuated alphaviruses. In accordance with these embodiments, one or more live, attenuated alphaviruses can be combined in a buffer having mannitol, histidine, and/or sucrose. In certain embodiments, a buffer such as a base buffer can include HEPES buffer. In accordance with these embodiments, buffered HEPES can be about pH 6.0 to about pH 10.0 having a concentration of about 1.0 to about 200.0 mM HEPES, histidine can be a concentration from about 0.1% to about 5.0% (w/v) (about 1 to about 50 mg/ml), sucrose can be about 0.1% to about 20% (w/v) (about 1 to about 200 mg/mL), and mannitol can be about 1.0% to about 15% (w/v) (about 1 to about 150 mg/mL) in the live, attenuated alphavirus compositions. In other embodiments, HEPES buffer concentrations can be from about 5.0 mM to about 50.0 mM, from about 10.0 mM to about 30 mM, or from about 10.0 mM to about 20 mM.

In certain embodiments, alphavirus formulations buffer can be about 15 mM HEPES buffer at pH from about 6.5 to about 8.0, from about 7.0 to about 7.5 or about 7.2 while histidine can be from about 5.0 mg/ml to about 20.0 mg/ml, sucrose can be from about 35.0 mg/ml to about 50.0 mg/ml, and mannitol can be from about 25.0 mg/ml to about 40.0 mg/ml in the live, attenuated alphavirus compositions. In other embodiments, formulations disclosed herein can include HEPES buffer having a concentration of about 15.0 mM solution at pH 7.2 while histidine can be about 5.0 mg/mL to about 12.5 mg/mL, sucrose can be about 35.0 mg/mL to about 50.0 mg/mL, and mannitol can be about 25.0 mg/mL to about 40.0 mg/mL in order to stabilize live alphaviruses or live attenuated alphaviruses.

In other embodiments, one or more live, attenuated alphaviruses can be combined with one or more agents that include, but are not limited to, sucrose, sodium chloride, monosodium glutamate, sodium phosphate, potassium phosphate and potassium chloride in order to stabilize the live, attenuated alphaviruses under various conditions. In accordance with these embodiments, a HEPES buffer can include, but is not limited to, one or more of sucrose having a concentration of about 1.0% to about 10.0% (w/v); sodium chloride having a concentration of about 0.05% to about 1.5% (w/v); monosodium glutamate having a concentration of about 0.05% to about 0.5% (w/v); sodium phosphate having a concentration of about 0.01 to about 0.15% (w/v); potassium phosphate having a concentration of about 0.01% to about 0.05% (w/v); and potassium chloride having a concentration of about 0.005% to about 0.05% (w/v) in combination with live alphaviruses or live, attenuated alphaviruses where the alphaviruses are stabilized and degradation of the alphaviruses are reduced.

In another embodiment, concentrations of sucrose can be about 5.0% (w/v); sodium chloride can be about 0.64% (w/v); monosodium glutamate can be about 0.1% (w/v); sodium phosphate can be about 0.09% (w/v); potassium phosphate can be about 0.016% (w/v); and potassium chloride can be about 0.016% (w/v) in combination with live alphaviruses where the live alphaviruses are stabilized and degradation is reduced and shelf-life is extended. Some embodiments disclosed herein are directed at methods for decreasing inactivation of live alphaviruses. In accordance with these embodiments, methods can include, but are not limited to, combining live alphaviruses with a composition that includes, but not limited to, 0.1 mM to 200.0 mM HEPES buffer, one or more carbohydrate agents (e.g. simple sugars, sugar alcohols and the like), and one or more amino acids. In accordance with these embodiments, HEPES buffer can be about pH 6.0 to pH 9.0 at a concentration from about 1.0 mM to about 200 mM, histidine can be about 0.1% to about 5.0% (w/v), sucrose can be about 0.1% to about 20% (w/v), and mannitol can be about 1.0% to about 10% (w/v), when combined with the live, attenuated alphavirus.

Some embodiments disclosed herein can be directed at methods for decreasing inactivation of live alphaviruses. In accordance with these embodiments, one or more live alphaviruses can be combined with compositions that include, but are not limited to, 0.1 to 200 mM HEPES buffer, one or more carbohydrate agents, and one or more salt agents. In accordance with these embodiments, sucrose concentration can be about 1.0% to about 10.0% (w/v); sodium chloride concentration can be about 0.1% to about 1.5% (w/v); monosodium glutamate concentration can be about 0.05% to about 0.5% (w/v); sodium phosphate concentration can be about 0.01 to about 0.15% (w/v); potassium phosphate concentration can be about 0.01% to about 0.05% (w/v); and potassium chloride concentration can be about 0.01% to about 0.05% (w/v) when combined with the live alphavirus in order to reduce degradation of the alphavirus. In another embodiment, sucrose concentration can be about 5.0% (w/v); sodium chloride concentration can be about 0.64% (w/v); monosodium glutamate concentration can be about 0.1% (w/v); sodium phosphate concentration can be about 0.09% (w/v); potassium phosphate concentration can be about 0.016% (w/v); and potassium chloride concentration can be about 0.016% (w/v) when combined with the live or live, attenuated alphavirus.

In certain embodiments, compositions disclosed herein can be used to reconstitute or rehydrate live alphaviruses that have been lyophilized. For example, after transporting of the dehydrated or lyophilized or frozen live alphaviruses at various temperatures from frozen to room temperature and the like. Compositions of use herein can increase stabilization and/or reduce inactivation and/or degradation of live or live, attenuated alphaviruses at various storage temperatures and during freeze-thaws cycles.

In certain embodiments, live or live, attenuated alphaviruses that can benefit from the compositions disclosed herein can include, but are not limited to, chikungunya virus (CHIK), o'nyong'nyong virus, Ross River virus, Eastern equine encephalitis, Venezuelan Equine Encephalitis Virus and Western equine encephalitis or other alphaviruses in the Coronaviridae and Togaviridae families. Other Semliki Forest virus complexes include, but are not limited to, Bebaru virus, Mayaro virus, Subtype: Una virus, O'Nyong Nyong virus: Subtype: Igbo-Ora virus, Ross River virus: Subtype: Bebaru virus; Subtype: Getah virus; Subtype: Sagiyama virus, and Semliki Forest virus: Subtype: Me Tri virus.

Other embodiments disclosed herein concern live, attenuated alphavirus compositions and methods directed to creating a vaccine or immunogenic compositions capable of reducing or preventing onset of a medical condition caused by one or more of the alphaviruses contemplated herein. In certain embodiments, one or more live, attenuated viruses of compositions contemplated herein can be part of a pharmaceutical composition and include a pharmaceutically acceptable excipient. Pharmaceutical compositions disclosed herein can be of use to reduce onset of an infection of an alphavirus and a condition caused by an alphavirus infection when the pharmaceutical composition is administered to a subject. A subject can be a mammal for example, a domesticated animal a pet, livestock, other animal or a human subject (an adult or child).

Other embodiments concern kits for decreasing the inactivation of a live, attenuated virus including, but not limited to, a container; and a composition disclosed herein

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein.

DESCRIPTION OF ILLUSTRATIVE EMBODIMENTS

Definitions

Figure 1:
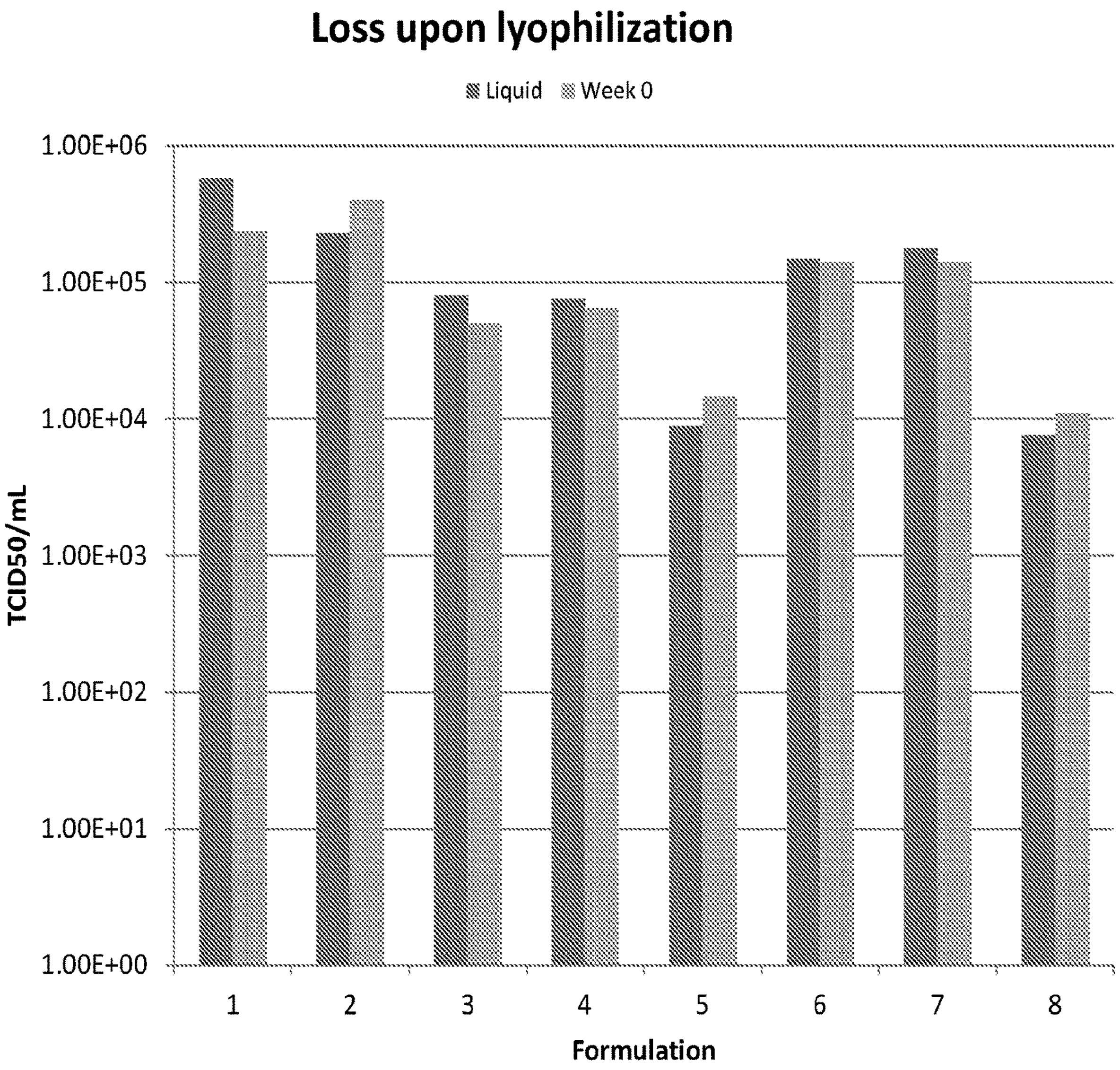
FIG. 1 is an exemplary histogram plot representing experiments using various liquid and lyophilized compositions for testing stability of exemplary live alphaviruses in one embodiment disclosed herein.

As used herein, “a” or “an” may mean one or more than one of an item.

As used herein, “about” may mean up to and including plus or minus five percent, for example, about 100 may mean 95 and up to 105.

As used herein CHIKV can mean Chikungunya Virus.

As used herein TCID50 can mean 50% Tissue Culture Infective Dose.

As used herein HB can mean HEPES Buffer Saline.

As used herein HBS can mean HEPES Buffer Saline+Sucrose.

As used herein DMEM can mean Dulbecco’s modified minimal essential medium.

As used herein PBS can mean Phosphate Buffered Saline.

As used herein FBS can mean Fetal Bovine Serum.

As used herein Lyo can mean lyophilized or dehydrated depending on the formulation of reference.

As used herein, “attenuated alphavirus” or “live, attenuated alphavirus” can mean an alphavirus that demonstrates reduced or no clinical signs of disease when administered to a subject (e.g. an animal or human).

DETAILED DESCRIPTIONS

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

In certain embodiments, stability of live, attenuated alphaviruses of use in immunogenic or vaccine formulations have been observed in various formulations disclosed herein. In some embodiments, formulations for increasing alphavirus stability by reducing loss of titer in liquid, frozen, lyophilized and re-constituted or re-hydrated live, attenuated alphaviruses have been demonstrated. In certain embodiments, live alphavirus formulations can include, but are not limited to, one or more live or live, attenuated alphaviruses, HEPES buffer, one or more amino acids, and one or more carbohydrate agents. In certain embodiments, compositions disclosed herein can include an alphavirus in a HEPES buffer, one or more amino acids that include histidine, and one or more carbohydrate agents that include at least one of sucrose and/or mannitol. Certain compositions disclosed herein can include salt or a salt solution. In accordance with these embodiments, formulations disclosed herein can be used for liquid, frozen or lyophilized storage of a live or live, attenuated alphavirus from about −80° C. to about 40° C. or above without significant loss of the alphavirus titer in the composition. In some embodiments, for example, long-term storage at 4° C. can be achieved using formulations disclosed herein. In certain embodiments, compositions contemplated herein can be partially or wholly dehydrated or hydrated.

In some embodiments, live alphaviruses or live, attenuated alphaviruses contemplated to benefit from compositions disclosed herein can include, but are not limited to, chikungunya virus (CHIK), o'nyong'nyong virus, Ross River virus, Eastern equine encephalitis, Venezuelan Equine Encephalitis Virus and Western equine encephalitis or other alphaviruses in the Coronaviridae and Togaviridae families. Other Semliki Forest virus complexes include, but are not limited to, Bebaru virus, Mayaro virus, Subtype: Una virus, O'Nyong Nyong virus: Subtype: Igbo-Ora virus, Ross River virus: Subtype: Bebaru virus; Subtype: Getah virus; Subtype: Sagiyama virus, and Semliki Forest virus: Subtype: Me Tri virus.

Certain embodiments disclosed herein concern chikungunya virus. Chikungunya virus is an alphavirus with a positive sense single-stranded RNA genome of approximately 11.6 kb. It is a member of the Semliki Forest Virus complex and is closely related to Ross River Virus, O'Nyong Nyong virus and Semliki Forest Virus. Compositions disclosed herein can be used to stabilize viruses of the Semliki Forest Virus complex variety by reducing degradation of live alphaviruses or live, attenuated alphaviruses.

In certain embodiments, a live, attenuated alphaviruses contemplated herein can include a chimeric alphavirus. In other embodiments, a live, attenuated alphavirus can include a live attenuated or a chimeric chikungunya virus. In accordance with these embodiments, one exemplary chimeric alphavirus is one that is capable of being expressed in mammalian cells and not in insect cells. In certain embodiments, a live, attenuated alphavirus can include a live, attenuated alphavirus that is incapable of replicating in mosquitoes and mosquito cells. In other embodiments, a live, attenuated alphavirus contemplated to benefit from compositions disclosed herein can be one that has been manipulated to be under eukaryotic control (e.g. insertion of a eukaryotic element such as a IRES sequence and/or inactivation of the subgenomic promoter of the alphavirus). In other embodiments, a live, attenuated alphavirus can include, an alphavirus nucleic acid, having (i) an insertion of an internal ribosomal entry site (IRES) between the end of nonstructural protein 4 (nsP4) coding sequence and initiating AUG of a subgenomic RNA coding sequence of the alphavirus, and (ii) an inactivated subgenomic promoter, wherein the alphavirus is attenuated. In certain embodiments, the IRES sequence can be an encephalomyelocarditis virus (EMCV) IRES or other similar IRES capable of creating a viable attenuated alphavirus construct of use in a vaccine composition.

Embodiments herein concern methods and compositions to reduce or prevent degradation and/or inactivation of live, attenuated alphaviruses. In accordance with these embodiments, certain compositions can include combinations of components that reduce degradation and/or inactivation of the live, attenuated alphavirus. Other embodiments herein concern combinations of agents capable of enhancing stability of live, attenuated alphaviruses. Yet other compositions and methods herein are directed to reducing the need for lower temperatures (e.g. refrigerated or frozen storage) while increasing the shelf life of aqueous and/or reconstituted live alphaviruses or live, attenuated alphaviruses.

In some embodiments, one or more live alphaviruses or live, attenuated alphaviruses can be combined with one or more amino acids and one or more carbohydrates. In certain embodiments, alphavirus formulations disclosed herein can include at least three components of HEPES buffer, carbohydrate(s) and an amino acid. In other embodiments, formulations for increasing stabilization of live alphaviruses disclosed herein can include compositions that do not contain human or mammalian derived agents such as protein (e.g. no serum or gelatins). In other embodiments, a salt agent can be added to these compositions in order to enhance buffering capacity or other desired property of the formulation.

Other embodiments disclosed herein concern live alphaviruses or live, attenuated alphavirus compositions for use in the preparation of immunogenic or vaccine compositions capable of reducing or preventing onset of an infection or side effect of exposure caused by one or more alphaviruses when administered to a subject. Subjects contemplated to benefit from these immunogenic or vaccine compositions include humans (e.g. adults, adolescents, children and infants) and animals such as pets, livestock or other domesticated or wild animals.

Some embodiments concern methods for decreasing inactivation of a live alphaviruses or live, attenuated alphaviruses including, but not limited to, combining one or more alphaviruses or live, attenuated alphaviruses with a composition capable of reducing inactivation of the alphaviruses including, but not limited to, one or more protein agents, one or more amino acids; one or more carbohydrate, one or more saccharides or polyols agents, and optionally, a HEPES buffer, wherein the composition decreases inactivation of the alphavirus. In accordance with these embodiments, the live attenuated virus can include particular alphaviruses, such as those having similar features as chikungunya (e.g. Semliki Forest complex viruses) and other alphaviruses having a similar genetic structure, structural and non-structural protein layout and/or secondary structure or the like to the alphavirus chikungunya.

In some embodiments, a carbohydrate of use in formulations disclosed herein can be a sugar or a polyol or sugar alcohol. In accordance with these embodiments, sugars can include, but are not limited to, monosaccharides, (e.g. glucose, galactose, ribose, mannose, rhamnose, talose, xylose or allose arabinose), disaccharides (e.g. trehalose, sucrose, maltose, isomaltose, cellibiose, gentiobiose, laminaribose, xylobiose, mannobiose, lactose, or fructose), trisaccharides (e.g. acarbose, raffinose, melizitose, panose, or cellotriose) or sugar polymers (e.g. dextran, xanthan, pullulan, cyclodextrins, amylose, amylopectin, starch, celloologosaccharides, cellulose, maltooligosaccharides, glycogen, chitosan, or chitin). Polyols can include, but are not limited to sugar alcohols such as mannitol, sorbitol, arabitol, erythritol, maltitol, xylitol, glycitol, glycol, polyglycitol, polyethylene glycol, polypropylene glycol, isomalt, hydrogenated starch hydrosylates and glycerol.

In certain embodiments, other carbohydrate agents of use in formulations disclosed herein can be contemplated of use in compositions herein can include, but are not limited to, sucrose, fructose, galactose, trehalose, mannitol, sorbitol, amylose, amylopectin, starch, cellulose, maltooligosaccharides, glycogen, chitosan, or chitin. In other embodiments, amino acids contemplated of use herein include at least histidine and optionally, glycine.

In some embodiments, HEPES buffer can have a pH of about pH 6.0 to about pH 10, a concentration from about 1.0 mM to about 200 mM, one or more amino acid concentration can be from about 1.0 mg/ml to about 40 mg/ml and the one or more carbohydrate agent concentration can be from about 1.0 mg/ml to about 100 mg/ml in the live, attenuated alphavirus compositions. In other embodiments, the HEPES buffer concentration can be from about pH 6.5 to pH 8.0 at a concentration of about 1.0 mM to about 40 mM, the one or more amino acid concentration can be from about 1.0 mg/ml to about 30 mg/ml and the one or more carbohydrate agent concentration can be from about 10 mg/ml to about 50 mg/ml in the live, attenuated alphavirus compositions.

In certain embodiments, live, attenuated alphaviruses compositions can include, but are not limited to, HEPES buffer, mannitol, histidine, and sucrose. In accordance with these embodiments, HEPES buffer can be a pH of about pH 6.0 to about pH 10.0 at a concentration of about 1.0 mM to about 200 mM, histidine can be a concentration of about 0.1% to about 5.0%, sucrose can be a concentration of about 0.1% to 20.0%, and mannitol can be a concentration of about 1.0% to about 10% and one or more live, attenuated alphaviruses. In certain embodiments, formulations can further include 10 mM to 150 mM salt (e.g. sodium chloride or other appropriate salt).

Some embodiments, directed to compositions and methods for decreasing inactivation of a live, attenuated alphavirus composition, can include, but are not limited to, combining one or live attenuated alphaviruses with a composition that includes, but not limited to, 0.1 mM to 200 mM HEPES buffer, one or more carbohydrate agents, and one or more amino acids. In accordance with these embodiments, concentrations of buffered HEPES can be about pH 6.0 to pH 10 at about 1 to about 200 mM, histidine can be about 0.1% to about 5.0%, sucrose can be about 0.1% to about 20%, and mannitol can be about 1.0% to about 10% when combined with the live, attenuated alphavirus. In some embodiments, the HEPES buffer can be about pH 6.0 to pH 10 at about 1 to about 40 mM while histidine can be about 5 mg/ml to about 50 mg/ml, sucrose can be about 5 mg/ml to about 50 mg/ml, and mannitol can be about 5 mg/ml to about 50 mg/ml when combined with the live, attenuated alphavirus. In other embodiments, HEPES buffer can be about pH 6.5 to pH 7.5 at about 1 to about 30 mM while histidine can be about 5 to about 30 mg/ml, sucrose can be about 10 to about 50 mg/ml, and mannitol can be about 5 to about 40 mg/ml when combined with the live, attenuated alphavirus. In other embodiments, the HEPES buffer can be about pH 7.2 at about 10 to 20 mM while histidine can be about 5 mg/ml to about 25 mg/ml, sucrose can be about 20 mg/ml to about 50 mg/ml, and mannitol can be about 10 mg/ml to about 40 mg/ml when combined with the live, attenuated alphavirus. In other embodiments, the HEPES buffer can be a 15 mM solution at pH 7.2 while histidine can be about 5 mg/ml to about 20 mg/ml, sucrose can be about 35 mg/ml to about 50 mg/ml, and mannitol can be about 25 mg/ml to about 40 mg/ml when combined with the live, attenuated alphavirus. In another embodiment, the HEPES buffer can be a 15 mM solution at pH 7.2 while histidine is about 5.0 mg/ml to 12.5 mg/mL, sucrose is about 35.0 mg/ml to about 50.0 mg/mL, and mannitol is about 25.0 mg/ml to about 40.0 mg/mL when combined with the live, attenuated alphavirus.

Some embodiments disclosed herein can be directed to compositions for decreasing inactivation of live alphaviruses or live, attenuated alphaviruses where the compositions and methods can include, but are not limited to, combining one or more alphaviruses with compositions that include, but are not limited to, 0.1 mM to 200 mM HEPES buffer, one or more carbohydrate agents, and one or more salt agents. In accordance with these embodiments, sucrose concentration can be about 1.0% to about 10.0% (w/v); sodium chloride concentration can be about 0.1% to about 1.5% (w/v); monosodium glutamate concentration can be about 0.05% to about 0.5% (w/v); sodium phosphate concentration can be about 0.01 to about 0.15% (w/v); potassium phosphate concentration can be about 0.01% to about 0.05% (w/v); and potassium chloride concentration can be about 0.01% to about 0.05% (w/v) in order to reduce degradation of the alphavirus. In another embodiment, sucrose concentration can be about 5.0% (w/v); sodium chloride concentration can be about 0.64% (w/v); monosodium glutamate concentration can be about 0.1% (w/v); sodium phosphate concentration can be about 0.09% (w/v); potassium phosphate concentration can be about 0.016% (w/v); and potassium chloride concentration can be about 0.016% (w/v) when combined with the live alphaviruses.

In certain embodiments, compositions disclosed herein can be used to rehydrate live alphaviruses that have been partially or completely lyophilized or to transport live alphaviruses at various temperatures from a variety of temperatures. Compositions contemplated herein can increase stabilization and/or reduce inactivation and/or degradation of a live, attenuated alphavirus at various storage temperatures, during processing, preparation or purification, during transport, delivery and during freeze-thaws cycles.

In certain embodiments, compositions contemplated herein can be partially or wholly dehydrated or hydrated. Further, compositions disclosed herein can be used during and after lyophilization of a live alphavirus. In accordance with these embodiments, a composition may be 20% or more; 30% or more; 40% or more; 50% or more; 60% or more; 70% or more; 80% or more; 90% or more; or 95% or more dehydrated. Compositions described herein are capable of increasing shelf-life of an aqueous or rehydrated live attenuated alphavirus. Further, compositions disclosed herein increase stability of live, attenuated alphavirus at a wide-range of temperatures such as room temperature, subzero temperatures, elevated temperatures (e.g. from −80° C. to 40° C. and above) under lyophilized or liquid/frozen conditions. In other embodiments, compositions disclosed herein can increase stability of a live alphavirus 1.5 times, 2 times, 2.5 times, 3 times, 3.5 times, 4 times or 10 fold or more than a live alphavirus not formulated in a composition of HEPES buffer, one or more carbohydrate agents, and one or more amino acids.

In other embodiments, methods disclosed herein can include freeze drying or other dehydrating methods to preserve alphaviruses in the disclosed compositions. In accordance with these embodiments, compositions disclosed herein are capable of decreasing inactivation of the freeze dried or partially or wholly dehydrated live alphavirus. In other methods, compositions for decreasing inactivation of a live alphavirus can include an aqueous composition or can include a rehydrated composition after dehydration. In certain embodiments, compositions disclosed herein are capable of increasing shelf-life of an aqueous or rehydrated alphavirus formulation by reducing degradation of the alphavirus.

In certain embodiments, compositions contemplated herein are capable of decreasing inactivation and/or degradation of a hydrated live attenuated alphavirus for greater than 12 to greater than 24 hours at room temperatures (e.g. about 20° C. to about 25° C. or even as high as 40° C.) or refrigeration temperatures (e.g. about 0° to about 10° C. or up to 20° C.). In some embodiments, compositions disclosed herein are capable of maintaining 90% or greater live attenuated alphaviruses for 24 hours or more. In addition, compositions disclosed herein are capable of reducing inactivation of a hydrated live alphavirus during at least 2, at least 3, at least 4, at least 5, at least 6 and more freeze-thaws cycles. Other embodiments concern compositions capable of reducing inactivation of hydrated or aqueous live alphaviruses for about 24 hours to greater than 26 weeks at refrigeration temperatures (e.g. about 0° to about 10° C.). Compositions contemplated in these methods, can include, but are not limited to, a HEPES buffer, histidine, sucrose, and mannitol. In certain embodiments, the live, alphavirus composition maintains about 100%, or about 90%, or about 80% or about 70% viral titer after greater than 24 hours at approximately 40° C. and greater than 90% viral titer after 4 weeks at refrigeration temperatures around 4° C. Other embodiments herein can include live alphavirus compositions maintaining about 90%, or about 80% viral or about 70% viral titer after 12 weeks at approximately 25° C. and about 90%, or about 80% viral titer or about 70% after about 26 weeks at refrigeration temperatures around 4° C. Other embodiments contemplated herein include live alphavirus compositions remaining at about 3 times to about 10 times the concentration of viral titer after several hours (e.g. 20 hours) at approximately 40° C. compared to other compositions known in the art.

In other embodiments, compositions contemplated herein can contain trace amounts or no divalent cations. For example, compositions contemplated herein can have trace amounts or no calcium/magnesium ($Ca^{+2}/Mg^{+2}$).

Formulations for other live, attenuated viruses have previously been described (see for example Burke, Hsu et al. 1999). One common stabilizer, referred to as SPGA is a mixture of 2 to 10% sucrose, phosphate, potassium glutamate and 0.5 to 2% serum albumin (see for example Bovarnick, Miller et al. 1950). Various modifications of this basic formulation have been identified with different cations, with substitutions of starch hydrolysate or dextran for sucrose, and with substitutions of casein hydrolysate or poly-vinyl pyrrolidone for serum albumin. Other formulations use hydrolyzed gelatin instead of serum albumin as a protein source (Burke, Hsu et al 1999). However, gelatin can cause allergic reactions in immunized children and adults and could be a cause of vaccine-related adverse events. Additionally, gelatin can be sourced from bovine or porcine bones and spinal material. These sources have been sources of extraneous agents (retroviruses and/or prions—BSE) and provide a safety concern. Additionally, albumin can be collected from humans—which also pose a potential risk of introducing unsafe extraneous agents. Therefore, one goal disclosed herein was to identify formulations that have equal to improved stabilizing effects on live, attenuated or live alphaviruses without the adverse allergic reactions or possible safety concerns in subjects to agents such as gelatin and/or serum albumin. In certain embodiments, formulations disclosed herein can be compared to formulations containing gelatin where the instant formulations demonstrate equal to superior stabilizing effects on alphaviruses without the adverse effects of gelatin-containing formulations.

Embodiments herein disclose compositions that enhance stability of and/or reduce deterioration or reduce the chance of allergic reaction of live alphavirus compositions compared to those in the prior art. Certain compositions disclosed herein provide stability of aqueous viruses for up to 1 day; up to 2 days; up to 4 days and greater than 6 weeks at or about 40° C. Certain compositions disclosed herein provide stability of aqueous viruses for up to 1 day to about 12 weeks or more, at or about room temperature (e.g. 25° C.). Embodiments disclosed herein increase protection of a live virus from for example, freezing and/or thawing, and/or elevated temperatures. In certain embodiments, compositions disclosed herein can stabilize, reduce deterioration and/or prevent inactivation of dehydrated live, attenuated viral products at room temperature conditions (e.g. about 25° C.). In other embodiments, compositions contemplated herein can stabilize, reduce deterioration and/or prevent inactivation of aqueous live, viral products at about 25° C. or up to or about 40° C. or higher. Compositions disclosed herein can facilitate storage, distribution, delivery and accurate administration of alphavirus vaccines in developed and underdeveloped regions.

Those of skill in the art will recognize that compositions or formulas disclosed herein relate to viruses that are either live or live and attenuated by any method, including but not limited to, cell culture passages/selection, reassortment, incorporation of mutations into infectious clones, reverse genetics, insertions, deletions, chimeric constructs other recombinant DNA or RNA manipulation. In addition, those skilled in the art will recognize that certain alphaviruses that can benefit from the protective effects of formulations disclosed herein can be engineered to express other proteins or RNA including, but not limited to, recombinant alphavirus constructs. These viruses can be used as vaccines for infectious diseases, vaccines to treat ore reduce the onset of oncological conditions, or alphaviruses for expressing proteins or RNA (e.g., gene therapy, antisense therapy, ribozyme therapy or small inhibitory RNA therapy) to treat or prevent a condition.

In some embodiments, compositions disclosed herein can contain one or more viruses with membrane envelopes (e.g., enveloped viruses) of the Togavirus, or Coronavirus, or any alphavirus of the Togavirus family. In other embodiments, compositions herein can contain one or more enveloped, positive strand RNA virus of the Togavirus, or Coronavirus families. In certain embodiments, compositions can contain one or more live, attenuated alphaviruses (e.g. Chikungunya, VEEV, EEEV or similar) having one or more insertion, deletion or mutation to induce attenuation of the virus for use in a vaccine composition.

In certain embodiments, live alphavirus compositions can include one or more live, attenuated alphavirus constructs or viruses described in U.S. App No. PCT/US2009/000458, Filed Jan. 23, 2009 entitled: ATTENUATED RECOMBINANT ALPHAVIRUSES INCAPABLE OF REPLICATING IN MOSQUITOES AND USES THEREOF and U.S. patent application Ser. No. 12/804,535 filed Jul. 23, 2010, both applications and continuations and divisionals thereof are incorporated by reference for all purposes in their entirety.

Pharmaceutical Compositions

Some embodiments herein relate to pharmaceutical compositions for live, attenuated viruses in aqueous or lyophilized form. Those of skill in the art will recognize that formulations that improve thermal viral stability and reduce freeze-thaw inactivation of pharmaceutical compositions disclosed herein can improve products that are in aqueous form, powdered, freeze-dried or lyophilized and prepared by methods known in the art. After reconstitution, such stabilized immunogenic compositions can be administered by a variety routes, including, but not limited to intradermal administration, subcutaneous administration, intramuscular administration, intranasal administration, pulmonary administration or oral administration.

In other embodiments, devices to deliver any pharmaceutical compositions disclosed herein are contemplated. In accordance with these embodiments, a variety of devices are known in the art for delivery of the vaccines or other immunogenic compositions including, but not limited to, syringe and needle injection, bifurcated needle administration, administration by intradermal patches or pumps, intradermal needle-free jet delivery (intradermal etc.), intradermal particle delivery, or aerosol powder delivery.

In certain embodiments, compositions disclosed herein typically include a physiologically acceptable buffer. In some embodiment, HEPES buffer was found to have unexpected stabilizing effect on the alphavirus compositions when compared to other buffers. In certain embodiments, a buffering media with pH greater than 6.0 to about pH 10 is contemplated; some live, attenuated or live viruses (e.g. alphaviruses) are unstable at low pH.

Embodiments herein provide for administration of compositions to subjects in a biologically compatible form suitable for pharmaceutical administration in vivo. “Biologically compatible form suitable for administration in vivo” can mean a form of the active agent (e.g. live, attenuated virus of certain embodiments) to be administered in which any toxic effects are outweighed by the therapeutic benefits of the active agent.

Administration of a therapeutically active amount of pharmaceutical compositions disclosed herein can be defined as an amount effective, at dosages and for periods of time necessary to achieve a desired result. For example, a therapeutically effective amount of a compound can vary according to factors such as the disease state, age, sex, and weight of the individual, and the ability formulations to elicit a desired response in the individual. Dosage regime can be adjusted to provide optimum therapeutic response of a particular individual.

In some embodiments, compositions (e.g. pharmaceutical) can be administered to a subject by any known manner, for example, subcutaneous, intramuscular, intravenous, intradermal, by oral administration, inhalation, transdermal application, intravaginal application, topical application, intranasal or rectal administration. In one embodiment, the compound may be administered intranasally, such as inhalation. In certain embodiments, immunogenic compositions disclosed herein can be administered subcutaneously or intradermally.

Compounds or active agents (e.g. live, attenuated alphaviruses) disclosed herein can be administered to a subject in an appropriate carrier or diluent, co-administered with the composition. The term “pharmaceutically acceptable carrier” as used herein is intended to include diluents such as saline and aqueous buffer solutions. The active agent may also be administered parenterally or intraperitoneally.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It may further be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Upon formulation, solutions can be administered in a manner compatible with the dosage formulation and in such amount as is therapeutically effective. The formulations are easily administered in a variety of dosage forms, such as the type of injectable solutions described above. In some embodiments, formulations disclosed herein can be administered before, during and/or after exposure to an alphavirus of the instant invention.

Kits

Other embodiments concerns kits for use with compositions and methods and disclosed herein. Compositions and live virus formulations may be provided in a kit for use in scientific studies or for delivery and/or use to administer to a subject. In accordance with these embodiments, kits can include, but are not limited to, a suitable container, alphaviruses or live, attenuated alphavirus compositions and one or more additional agents such as other anti-viral agents, anti-fungal or anti-bacterial agents.

In other embodiments, kits can further include a suitably aliquoted alphavirus composition disclosed herein. In addition, compositions herein can be partially or wholly dehydrated or aqueous. Kits contemplated herein may be stored at room temperatures or at refrigerated temperatures as disclosed herein depending on the particular formulation.

In other embodiments, kits can generally include at least one vial, test tube, flask, bottle, syringe or other container, into which a composition can be placed, and suitably aliquoted. Where an additional component is provided, kits can also generally contain one or more additional containers into which this agent or component may be placed. Kits herein can also include containing a composition and any other reagent in containers for commercial sale. Such containers may include injection or blow-molded plastic containers into which the desired vials are retained (e.g. immunogenic or vaccine compositions).

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

Example 1

Buffer Screen

In certain exemplary methods, liquid composition and lyophilizable compositions suitable for preclinical and clinical testing and use of alphavirus immunogenic compositions or vaccines are identified. One consideration regarding a liquid composition in accordance with these exemplary compositions is that some alphaviruses are pH sensitive (e.g. to low pH). Therefore, components of a compositions disclosed herein include careful considerations regarding pH. In certain exemplary compositions, the pH of the formulations was about pH 6.0 to about 10.0 having several formulations maintained around pH 6.5 to 7.5.

In some methods, live, attenuated Chikungunya viruses (CHIK) are used as an example of an alphavirus composition for pre-clinical and clinical testing. Compositions for these methods are provided. In one exemplary experiment, a predetermined amount of CHIK-IRES vaccine (pMVS), a live, attenuated chikungunya virus with the structural genes under the control an inserted IRES is used. It is contemplated that any attenuated or live alphavirus can be used in these exemplary compositions to increase stability of the alphavirus and reduce degradation. Initially, many different buffers were tested such as DMEM, PBS, HEPES and others.

In other exemplary methods, certain tests were performed, such as incubation for up to 6 weeks at 40° C. to test stability of the live, attenuated viruses. Samples were taken to titrate for the presence of infectious virus by $TCID_{50}$ in 96 well plates on Vero cells. A percentage of the remaining virus as compared to an input (un-incubated) alphavirus composition control was calculated. Incubation of $10^5$ $TCID_{50}$ of for example, a live alphavirus containing PBS alone, 20% FBS DMEM or DMEM buffered Dextrose demonstrated a rapid loss in potency of the alphavirus (e.g. CHIK). Certain exemplary compositions were demonstrated to be effective at stabilizing live attenuated alphaviruses such as live, attenuated alphaviruses (e.g. CHIK), for example, a composition containing HEPES buffer (4-(2-hydroxyethyl)-1-piperazineethanesulfonic acid) (data not shown) at about 1.0 to about 200 mM HEPES. In one example, a composition containing 15 mM HEPES (HEPES Buffer Saline—HS) and 150 mM NaCl was found to provide increased stability to the attenuated alphavirus vaccine when compared to a control (data not shown).

Example 2

Screening for Stabilizing Formulations Absent Protein Allergens

In certain methods, some formulations use hydrolyzed gelatin instead of serum albumin as a protein source (Burke, Hsu et al 1999) and previously presented inventions related to the instant invention. However, gelatin, while providing stability to the live, attenuated viruses, can cause allergic reactions when administered to a subject and can sometimes be a cause of vaccine-related adverse events. Certain compositions disclosed herein can include combinations of components that provide comparable outcomes as those containing gelatin to reduce deterioration of live, attenuated alphaviruses while providing formulations having reduced allergic reactions when administered to a subject.

In some examples, formulations having no albumin or gelatin that can provide comparable or even increased stability to live alphaviruses or live, attenuated alphaviruses are described. These formulations include, but are not limited to, HEPES buffer, one or more carbohydrate agents, one or more amino acids, one or more protein agents, and/or one or more salt agents.

Exemplary Formulations are provided below (all formulations tested below were about pH 7.2+/−0.2):

I. 150 mM HEPES, 5% Sucrose, 1% Gelatin, and 0.9% Sodium Chloride (positive control) It was demonstrated that 15.0 mM and 150.0 mM HEPES behaved similarly for stabilizing alphaviruses.
II. 7% Sucrose, 3% Human Serum Albumin, and 1.5% Mannitol (protein containing, potential allergen)
III. 2.5% Sucrose, and 3% Histidine
IV. 1.5% Sucrose, and 2% Glycine
V. 1.5% Sucrose, 2% Glycine, 0.44% Sodium Chloride
VI. 2% Sucrose, 4% Mannitol, 0.5% Histidine
VII. 5% Sucrose, 0.64% Sodium Chloride, 0.1% Monosodium Glutamate, 0.09% Sodium Phosphate, 0.016% Potassium Phosphate, and 0.016% Potassium Chloride
VIII. 2.5% Mannitol, and 4.5% Peptone

TABLE 1

Stability Study Designs

| | weeks | | | | | | |
|---|---|---|---|---|---|---|---|
| | 0 | 1 | 2 | 4 | 8 | 12 | 26 |
| 4° C. | x | x | x | x | x | x | x |
| 25° C. | x | x | x | x | x | x | |
| 40° C. | x | x | x | x | | | |

Live, attenuated alphavirus samples formulated in these compositions were stored at controlled temperatures. 18, 15 and 9 samples per formulation were stored at each of 4° C., 25° C., and 40° C. respectively. Samples were observed for potency evaluation at the time points indicated in Table 1 and in exemplary FIGS. 3-5. Samples incubated at 25° C. and 4° C. (FIGS. 4-5, respectively) were analyzed in parallel with samples incubated at 40° C. (FIG. 3) in order to observe stability trends over a 4 to 26 week period.

Table 2 represents a compilation of exemplary outcomes from experiments using formulations I-VIII at week 0. Physiological features such as average resuspension time, pH, cake appearance score, appearance description, predicted osmosis, and residual moisture were measured recorded for each formulation. Formulations I, II, and VIII contain protein agents (e.g., gelatin, albumin, and peptone) and were used as controls and compared to formulations not containing protein agents. For example, formulations III, VI, and VII do not contain protein and exhibited cake appearance scores of higher than 3 and had residual moisture percentage between about 0.47% and about 1.15%.

TABLE 2

List of Formulations for Study I

| Formulation | Average Resuspension Time (sec) | Average pH | Cake Appearance Score | Description | Predicted Osm/L | Residual Moisture % |
|---|---|---|---|---|---|---|
| Formulation I: Sucrose/Gelatin/Hepes Buffer/Sodium Chloride (Control) | 86 | 7.12 | 3 | Shrinking on sides and bottom | 352 | 1.79 |
| Formulation II: Sucrose/Human Serum Albumin/Mannitol | 17 | 6.81 | 5 | Whole | 283 | 0.77 |
| Formulation III: Sucrose/Histidine | 21 | 7.51 | 3 | Cracked | 292 | 1.04 |
| Formulation IV: Glycine/Sucrose | 17 | 7.45 | 1 | Powder | 311 | 2.21 |
| Formulation V: Glycine/Sucrose/Sodium Chloride | 26 | 7.09 | 1 | Small Spheres | 388 | 3.21 |
| Formulation VI: Sucrose/Mannitol/Histidine | 28 | 7.46 | 4 | Melting on bottom | 310 | 0.47 |
| Formulation VII (SPG): Sucrose/Gelatin/Sodium Chloride/Monosodium Glutamate/Sodium Phosphate/Potassium Phosphate/Potassium Chloride | 26 | 6.99 | 5 | Whole | 273 | 1.15 |
| Formulation VIII: Mannitol/Peptone | 31 | 7.30 | 4 | Shrinking on sides, beige | 287 | 0.71 |

Example 3

Liquid and Lyophilized Formulations

Figure 2:
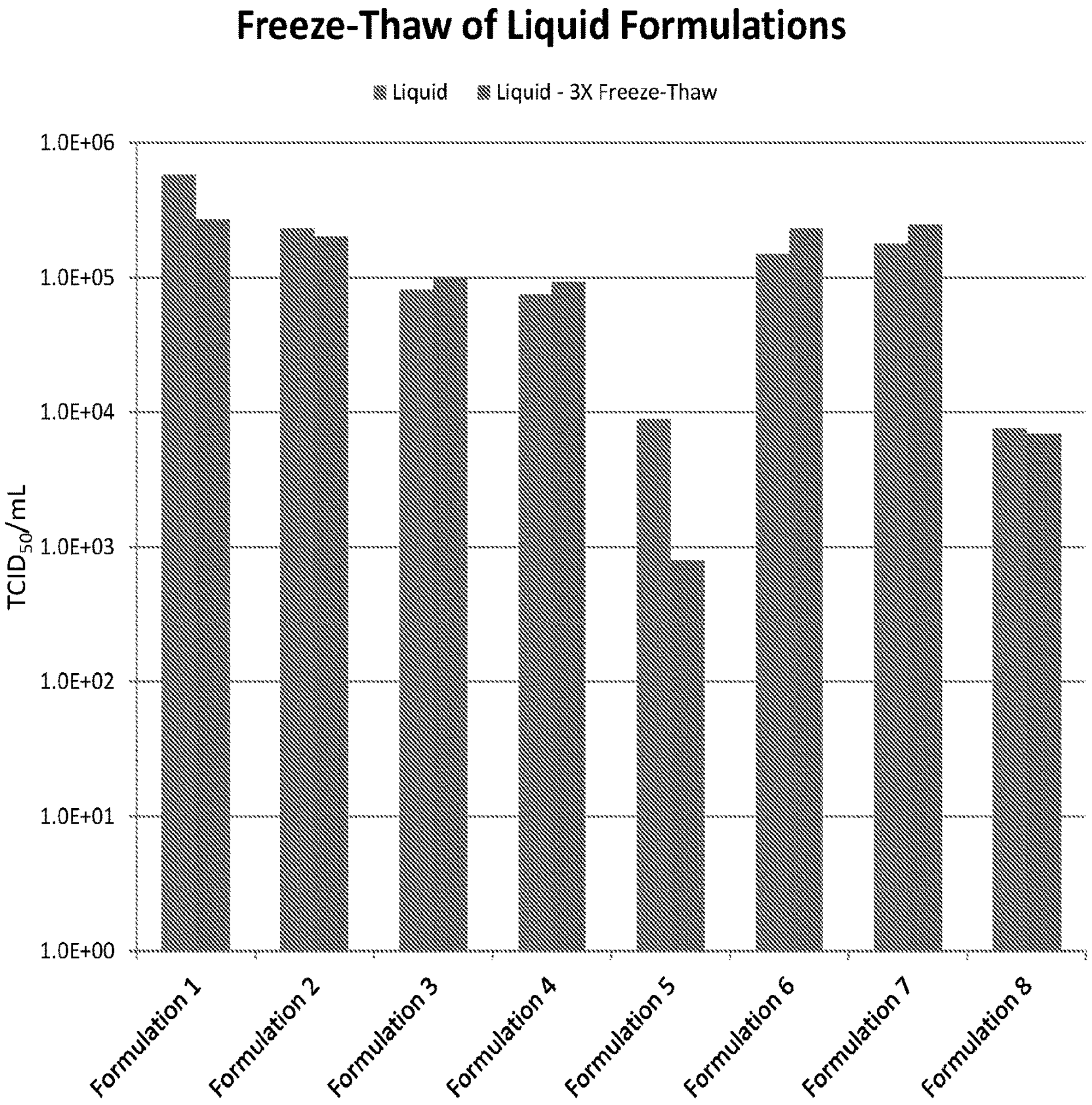
FIG. 2 is an exemplary histogram plot representing experiments using various liquid compositions for testing stability of exemplary live alphaviruses in one embodiment disclosed herein after freeze-thaw treatment.
Figure 3:
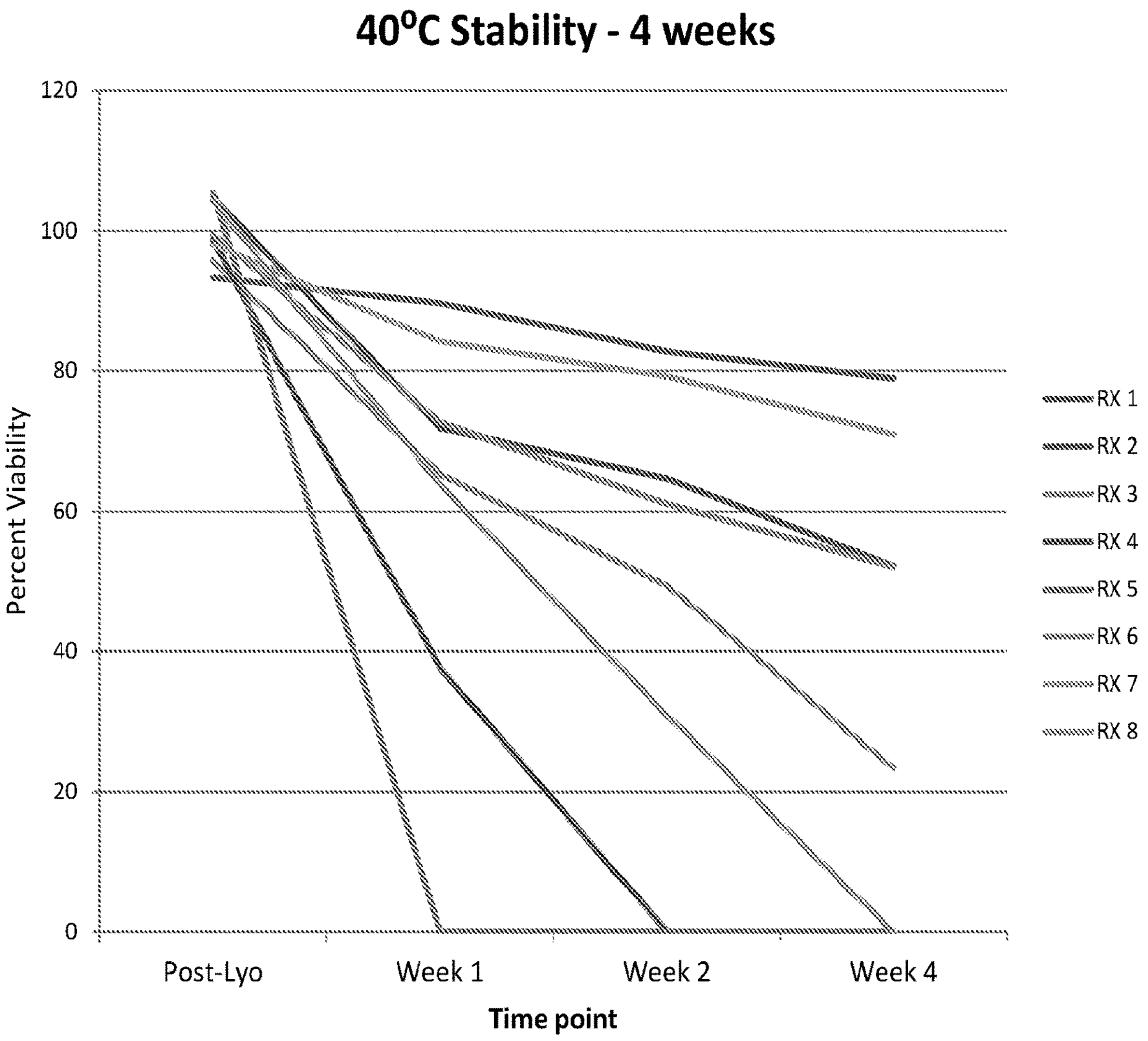
FIG. 3 is an exemplary graph representing experiments using various compositions for testing stability of exemplary live alphaviruses in one embodiment disclosed herein at about 40° C.
Figure 4:
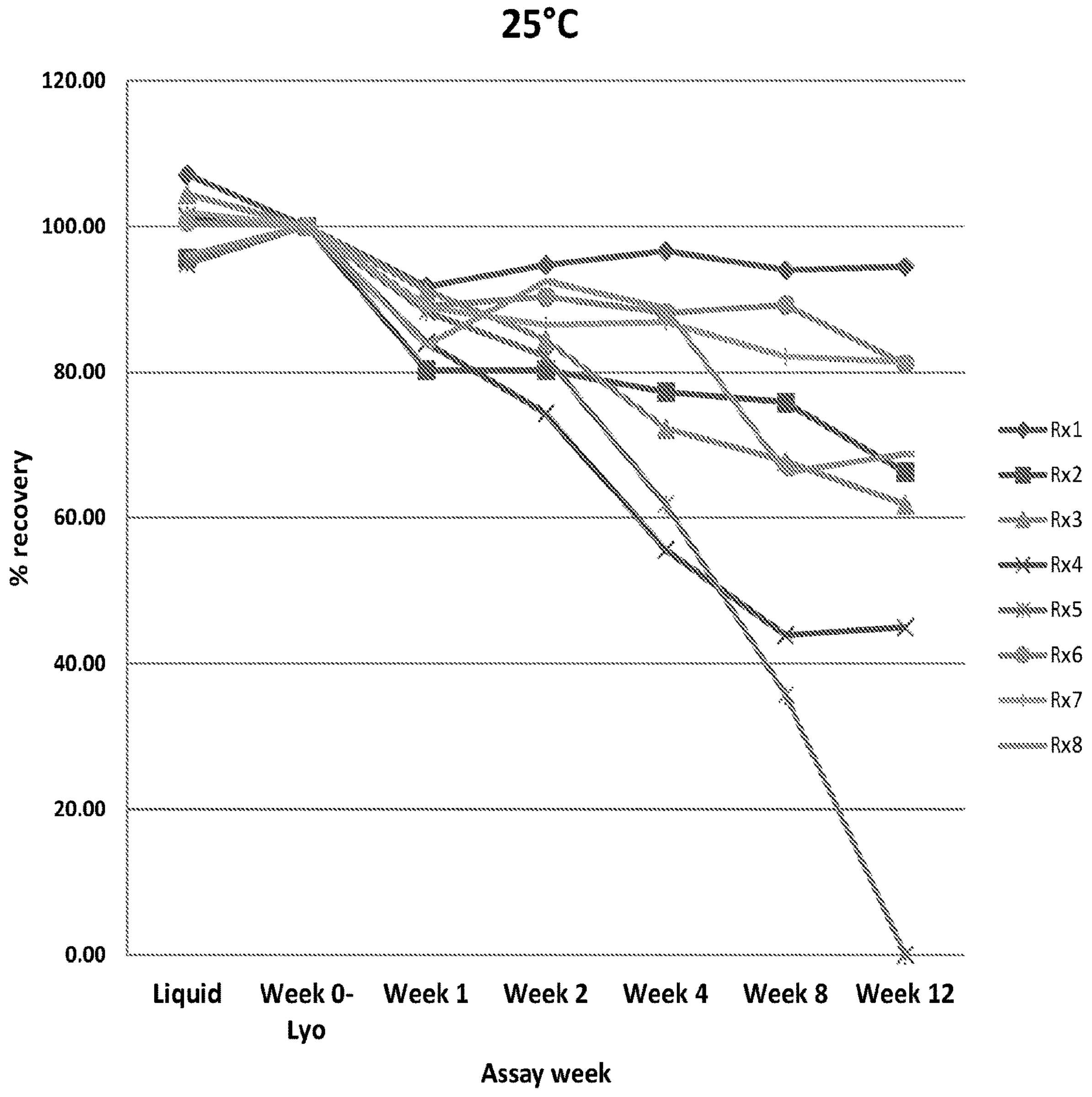
FIG. 4 is an exemplary graph representing experiments using various compositions for testing stability of exemplary live alphaviruses in one embodiment disclosed herein at about 25° C.
Figure 5:
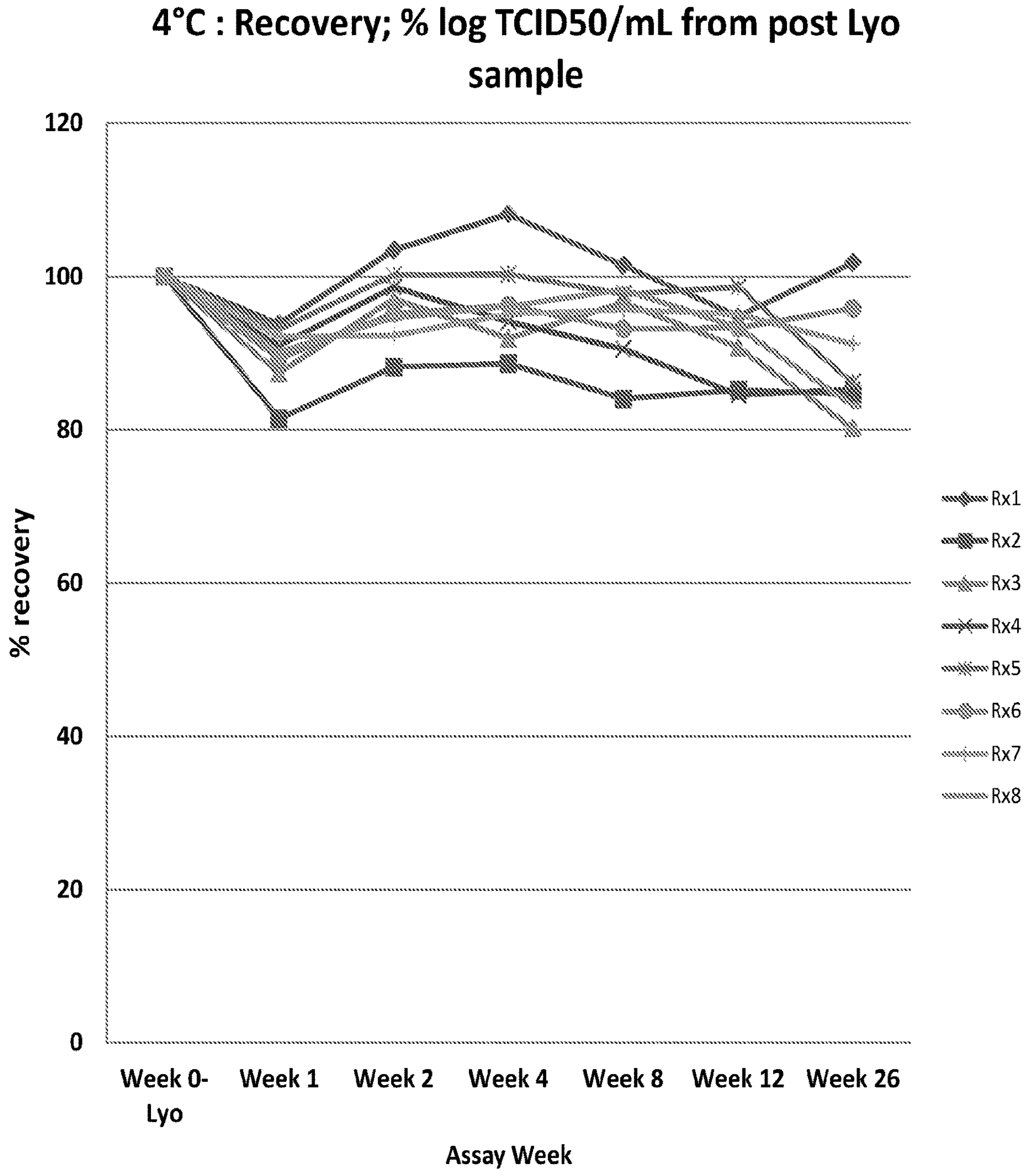
FIG. 5 is an exemplary graph representing experiments using various compositions for testing stability of exemplary live alphaviruses in one embodiment disclosed herein at about 4° C.

In other exemplary methods, stability of lyophilized attenuated alphavirus formulations (e.g. CHIK) were evaluated. None of the formulations lost significant titer upon lyophilization at week 0. However, formulations V and VIII lost significant titer upon processing (see FIG. 1), an indicator of liquid stability. Further, formulation V exhibited significant loss of titer upon freeze-thaw cycle of liquid formulations (FIG. 2). The lyophilized formulations I-VIII were stored at 40° C. (FIG. 3), 25° C. (FIG. 4), or 4° C. (FIG. 5). Samples taken at the indicated time points were reconstituted and titrated in Vero cells by $TCID_{50}$. The exemplary alphavirus formulation (e.g. live, attenuated CHIK formulation) VI (2% sucrose, 4% mannitol, 0.5% histidine) and formulation VII (5% sucrose, 0.64% sodium chloride, 0.1% monosodium glutamate, 0.09% sodium phosphate, 0.016% potassium phosphate, and 0.016% potassium chloride) demonstrated stabilizing features that are comparable to that of control formulations I and II for 4 weeks at 40° C. (FIG. 3). These formulations also demonstrated minimal loss of virus titer for greater than 12 weeks at 25° C. and at 4° C. (FIGS. 4 and 5).

Figure 6:
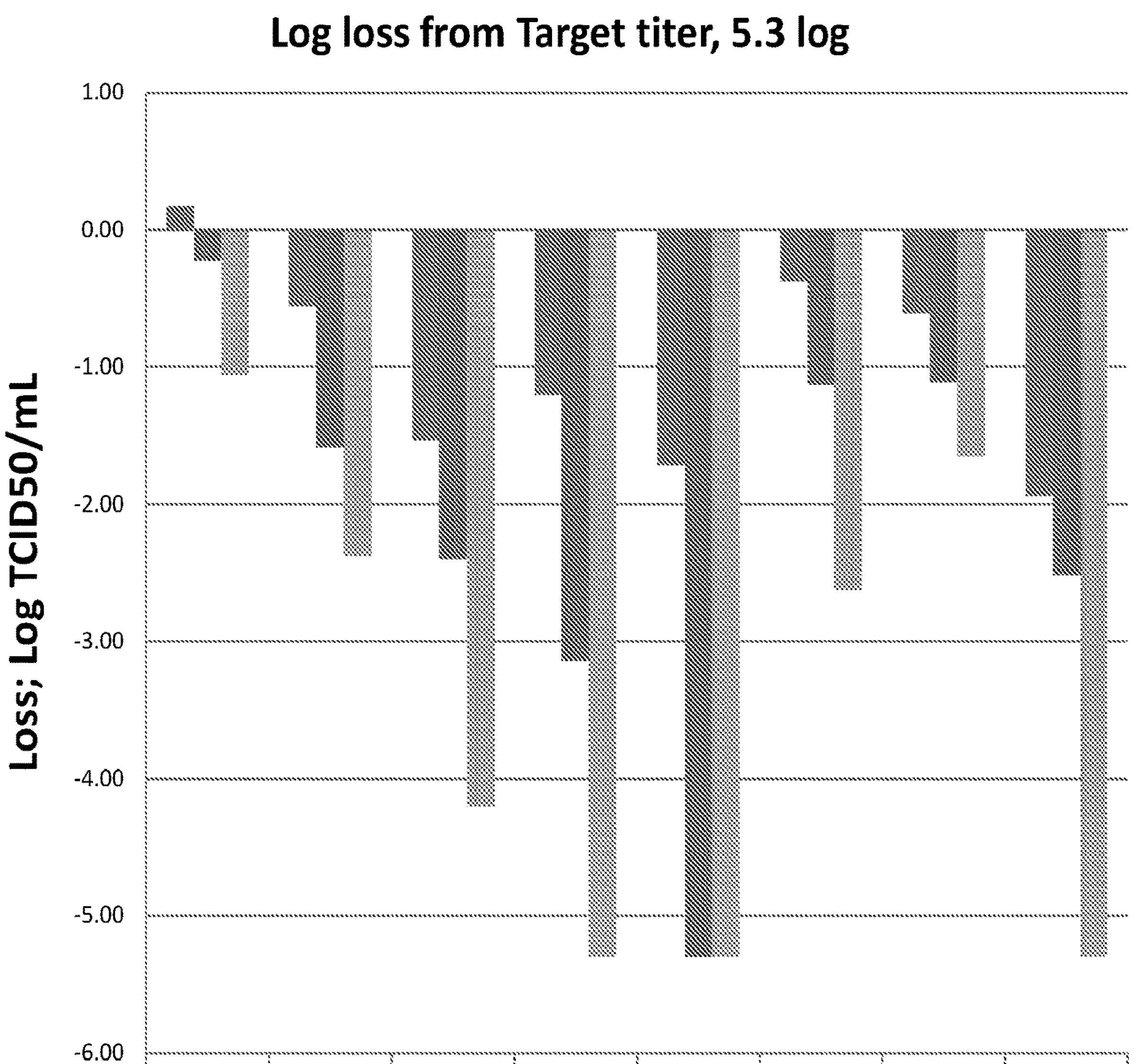
FIG. 6 is a histogram plot representing a cumulative overview of experiments using various compositions for testing stability of exemplary live alphaviruses in one embodiment disclosed herein at various temperatures.
Figure 7:
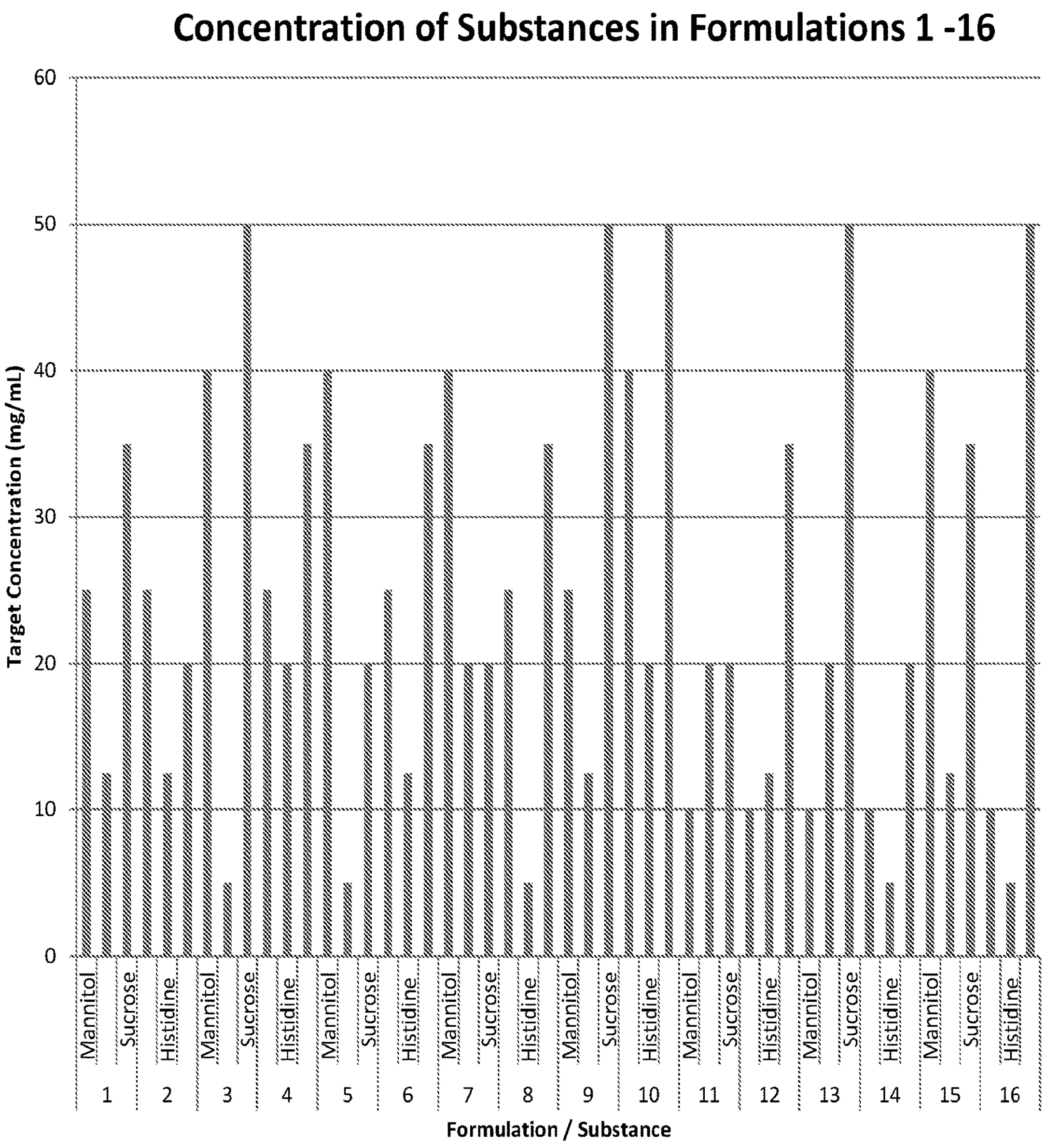
FIG. 7 is a histogram representing concentration ranges of various agents of use in one embodiment disclosed herein where the agents included in these exemplary compositions for stabilizing live alphaviruses are mannitol, histidine and sucrose.

FIG. 6 is a histogram plot illustrating loss of titer during accelerated and real-time stability experiments. All formulations tested provided stability to the live, attenuated virus from week 1 to week 26 at 4° C., but formulations IV, V, and VIII lost significant titer after 4 weeks at 40° C. Formulations VI and VII provided stabilizing compositions to the live, attenuated viruses at 40° C., 25° C., and 4° C. Formulation VI (2% sucrose, 4% mannitol, 0.5% histidine) was selected as a formulation candidate for additional evaluation and expansion.

Example 4

Stabilizing Formulations Absent Human and Mammalian Protein Agents

In other exemplary methods, long term stability experiments at 40° C., 25° C., and 4° C. were performed to analyze effects of varying concentrations of carbohydrates (e.g. sucrose and mannitol) and amino acids (e.g., histidine) on live, attenuated alphavirus stability, for example live, attenuated CHIK was used, based on observations that formulations having one or more carbohydrates and one or more amino acids had a positive effect on CHIK stability (see above). Using formulation VI presented above as a base formulation, formulations with varying concentrations of sucrose, mannitol, and histidine were formulated in a 15 mM HEPES buffer at pH 7.2+/−0.2.

Exemplary Formulations:

1. 15.0 mM HEPES, 25.0 mg/ml Mannitol, 12.5 mg/ml Histidine, and 35.0 mg/ml Sucrose
2. 15.0 mM HEPES, 25.0 mg/ml Mannitol, 12.5 mg/ml Histidine, and 20.0 mg/ml Sucrose
3. 15.0 mM HEPES, 40.0 mg/ml Mannitol, 5.0 mg/ml Histidine, and 50.0 mg/ml Sucrose
4. 15.0 mM HEPES, 25.0 mg/ml Mannitol, 20.0 mg/ml Histidine, and 35.0 mg/ml Sucrose
5. 15.0 mM HEPES, 40.0 mg/ml Mannitol, 5.0 mg/ml Histidine, and 20.0 mg/ml Sucrose (equivalent to Formulation VI discussed above)
6. 15.0 mM HEPES, 25.0 mg/ml Mannitol, 12.5 mg/ml Histidine, and 35.0 mg/ml Sucrose
7. 15.0 mM HEPES, 40.0 mg/ml Mannitol, 20.0 mg/ml Histidine, and 20.0 mg/ml Sucrose
8. 15.0 mM HEPES, 25.0 mg/ml Mannitol, 5.0 mg/ml Histidine, and 35.0 mg/ml Sucrose
9. 15.0 mM HEPES, 25.0 mg/ml Mannitol, 12.5 mg/ml Histidine, and 50.0 mg/ml Sucrose
10. 15.0 mM HEPES, 40.0 mg/ml Mannitol, 20.0 mg/ml Histidine, and 50.0 mg/ml Sucrose
11. 15.0 mM HEPES, 10.0 mg/ml Mannitol, 20.0 mg/ml Histidine, and 20.0 mg/ml Sucrose
12. 15.0 mM HEPES, 10.0 mg/ml Mannitol, 12.5 mg/ml Histidine, and 35.0 mg/ml Sucrose
13. 15.0 mM HEPES, 10.0 mg/ml Mannitol, 20.0 mg/ml Histidine, and 40.0 mg/ml Sucrose
14. 15.0 mM HEPES, 10.0 mg/ml Mannitol, 5.0 mg/ml Histidine, and 20.0 mg/ml Sucrose
15. 15.0 mM HEPES, 40.0 mg/ml Mannitol, 12.5 mg/ml Histidine, and 35.0 mg/ml Sucrose 16. 15.0 mM HEPES, 10.0 mg/ml Mannitol, 5.0 mg/ml Histidine, and 40.0 mg/ml Sucrose
17. (Positive Control) 15.0 mM HEPES Buffered saline containing sucrose and gelatin (HSG) 15.0 mM HEPES, 5% Sucrose, 1% Gelatin, and 0.9% Sodium Chloride. It was demonstrated that 15.0 mM and 150.0 mM HEPES behaved similarly for stabilizing alphaviruses.

TABLE 3

| Stability Designs | | | | | | |
|---|---|---|---|---|---|---|
| | weeks | | | | | |
| | 0 | 2 | 4 | 6 | 8 | 12 |
| 4° C. | x | x | x | | x | x |
| 25° C. | x | x | x | | x | x |
| 40° C. | x | x | x | x | | |

Figure 10:
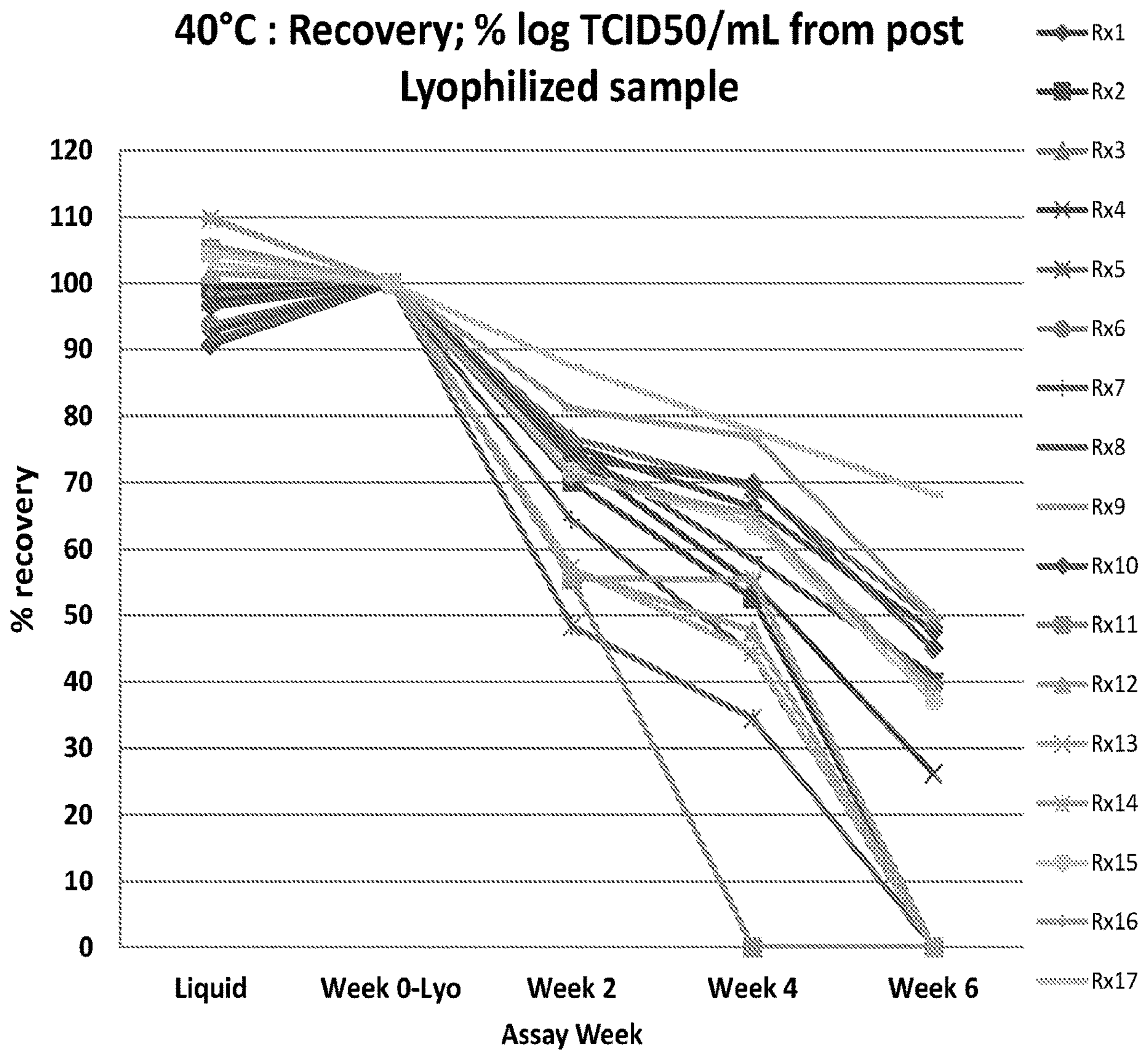
FIG. 10 is an exemplary graph representing experiments for testing stability of live alphaviruses in various formulations in one embodiment disclosed herein at about 40° C.
Figure 11:
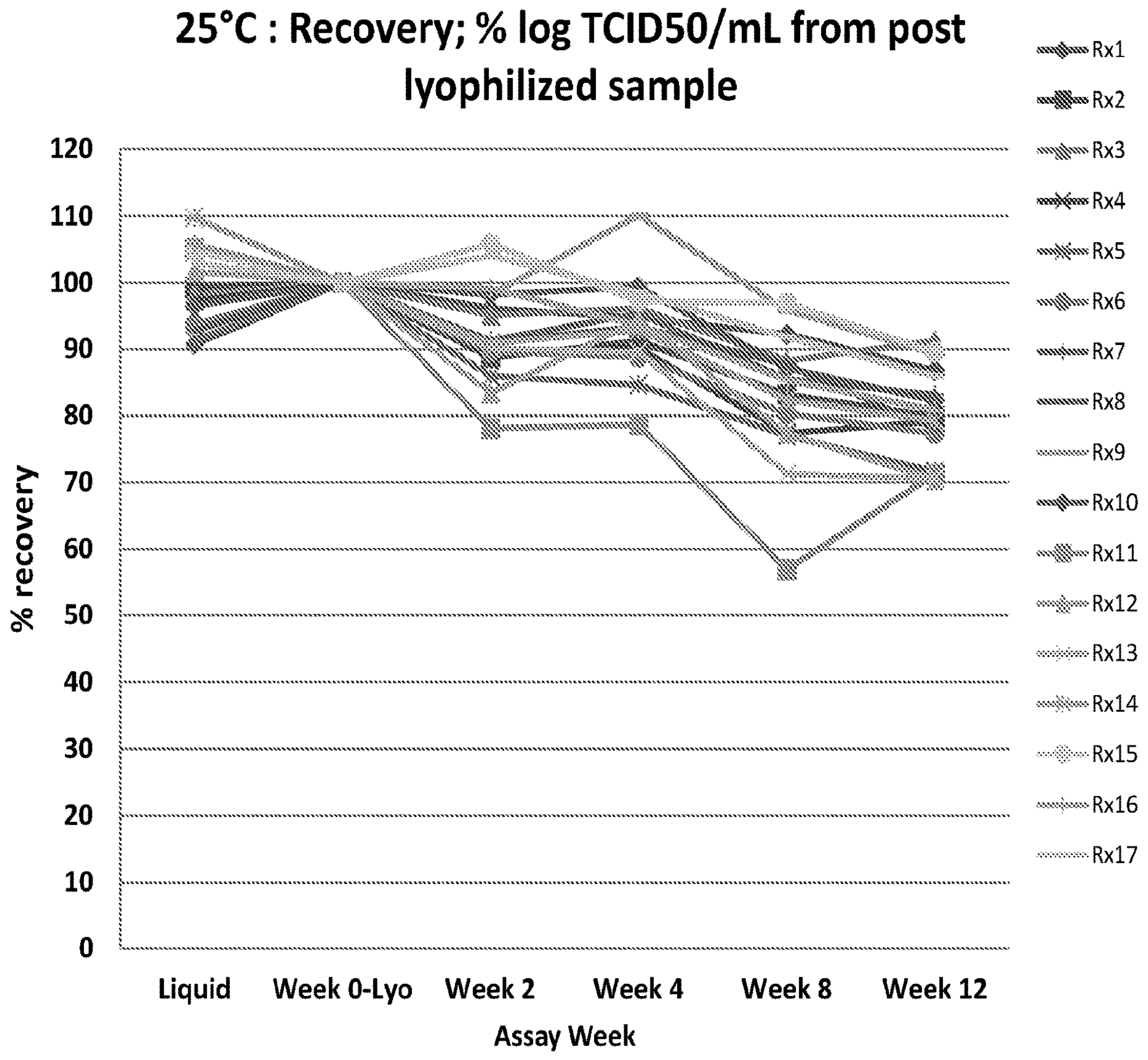
FIG. 11 is an exemplary graph representing experiments for testing stability of live alphaviruses in various formulations in one embodiment disclosed herein at about 25° C.
Figure 12:
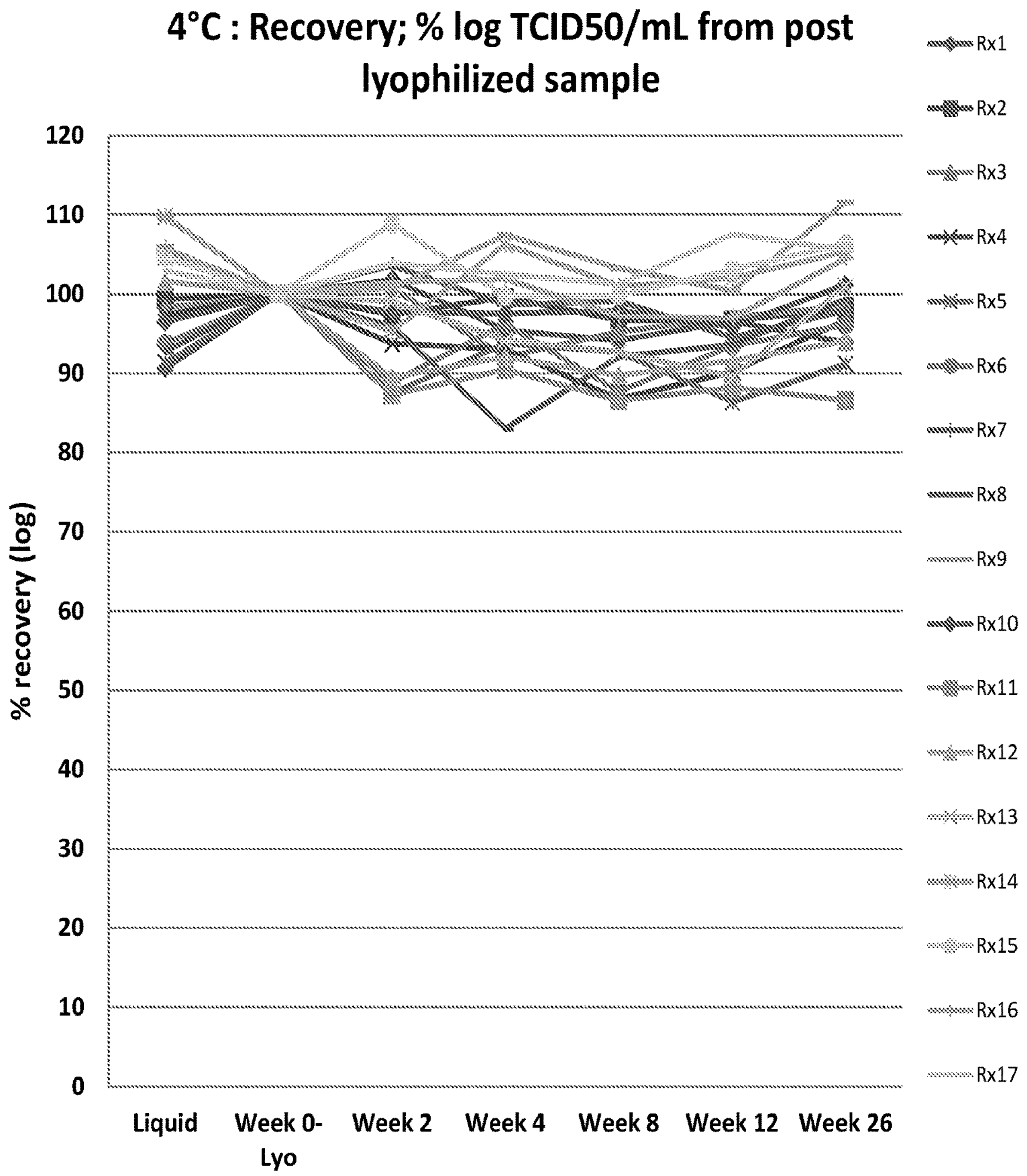
FIG. 12 is an exemplary graph representing experiments for testing stability of exemplary live alphaviruses in various formulations in one embodiment disclosed herein at about 4° C. or about refrigeration temperature.

Live, attenuated alphavirus samples formulated in these compositions were stored. 15 samples per formulation were stored at 4° C., 25° C., or 40° C. Samples formulations were studied for potency evaluation at the time points indicated in Table 3 and are exemplary results are illustrated in FIGS. 10-12. Samples incubated at 4° C. and 25° C. (FIGS. 11-12) were analyzed in parallel with samples incubated at and 40° C. (FIG. 10) to demonstrate the trend of titer remaining over 12 and 6 week periods, respectively.

Example 5

Liquid and Lyophilized Formulations

In another exemplary method, stability of lyophilized live, attenuated alphaviruses (e.g. CHIK) was evaluated. At week 0, all compositions 1-16 were analyzed for physiological features and exhibited cake appearance scores of higher than 3 and had residual moisture percentage between about 0.46% and about 1.46% (data not shown).

Figure 8:
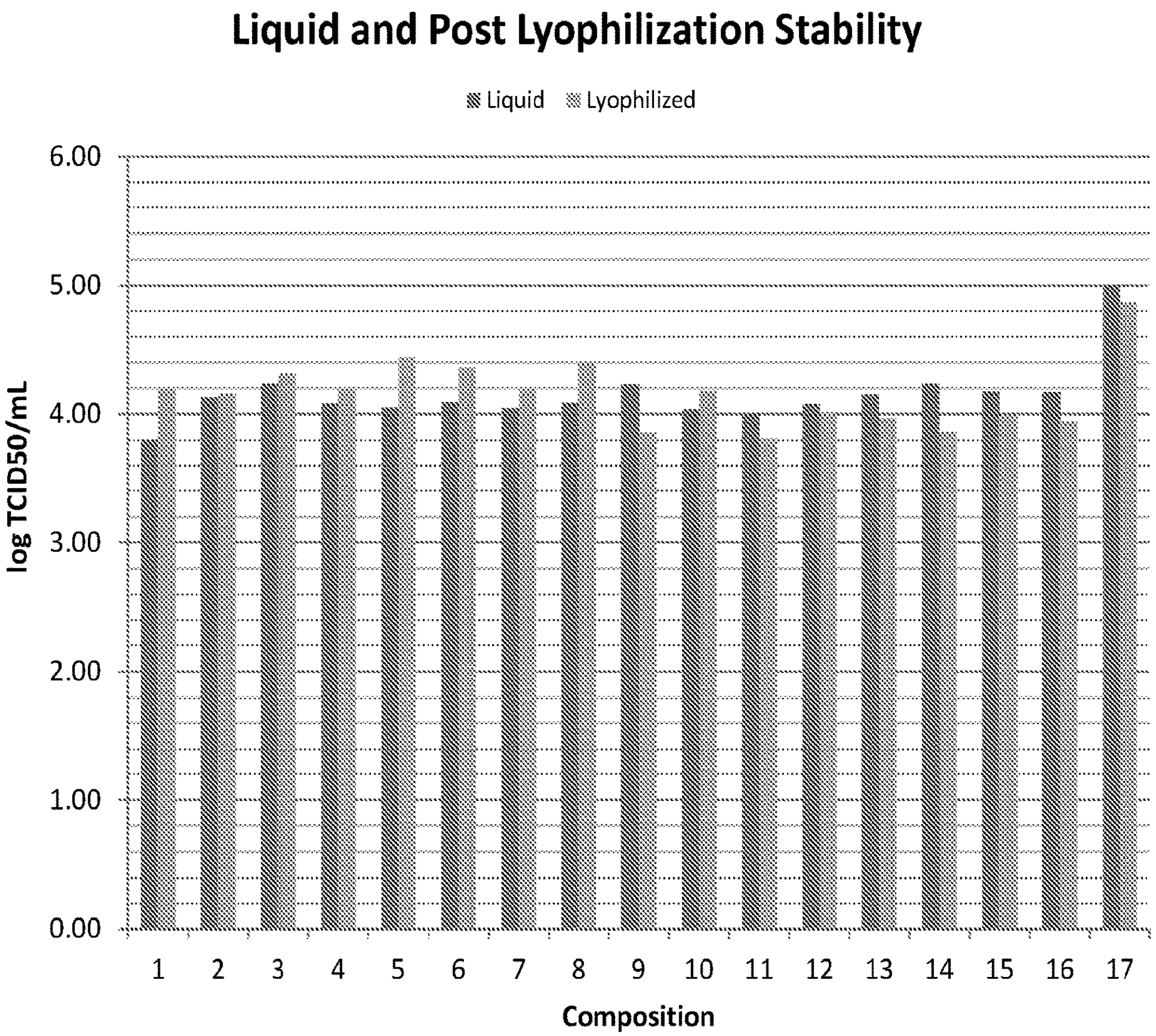
FIG. 8 is a histogram representing experiments using various compositions disclosed herein in liquid and lyophilized states for testing effects on live alphaviruses in one embodiment disclosed herein.
Figure 9:
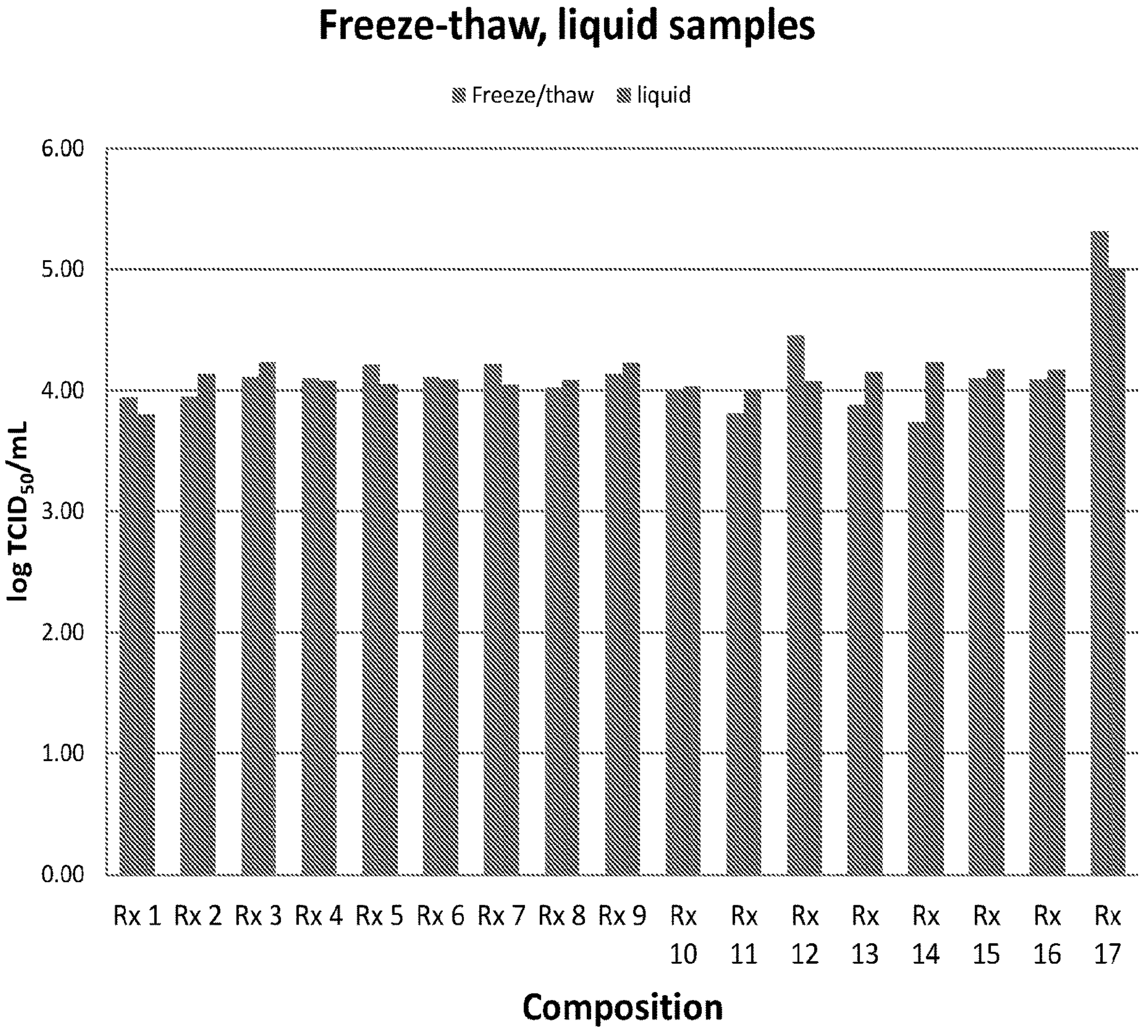
FIG. 9 is a histogram representing experiments using various compositions disclosed herein under freeze-thaw conditions for testing effects on live alphaviruses in one embodiment disclosed herein.

Some of these formulations exhibited higher remaining titers when lyophilized at week 0 (FIG. 8). Some of these formulations exhibited higher remaining titers upon freeze-thaw cycle (FIG. 9). In other experiments, lyophilized vaccine formulations 1-16 were stored at 40° C. (FIG. 10), 25° C. (FIG. 11), or 4° C. (FIG. 12) and assessed for overall titer loss at the various temperatures. Samples taken at the indicated time points were reconstituted and titrated in Vero cells using indicators to calculate $TCID_{50}$. Exemplary live alphaviruses (e.g. live, attenuated CHIK) formulations 1, 3, 9, an 10 of this test group compared to positive control 17 were found to be stable for up to at least 6 weeks at 40° C. with >45% recovery while other formulations 2, 5, 7, 11, 12, 13, 14 exhibited reduced recovery at least to 6 weeks when stored at room temperature, about 40° C. (FIG. 10) when compared to 1, 3, 9, 10 and control formulation 17. Formulations 1, 3, 9, and 15 compared to positive control formulation 17 were stable for at least 12 weeks when stored at about 25° C. while formulations 5, 11, and 13 had significant titer loss after about 8-12 weeks at 25° C. (FIG. 11). In spite of this comparible loss at 25° C., all formulations tested (1-16) demonstrated minimal loss of virus titer for greater than 12 weeks when stored at refrigeration temperatures of about 4° C. (FIG. 12).

Figure 13:
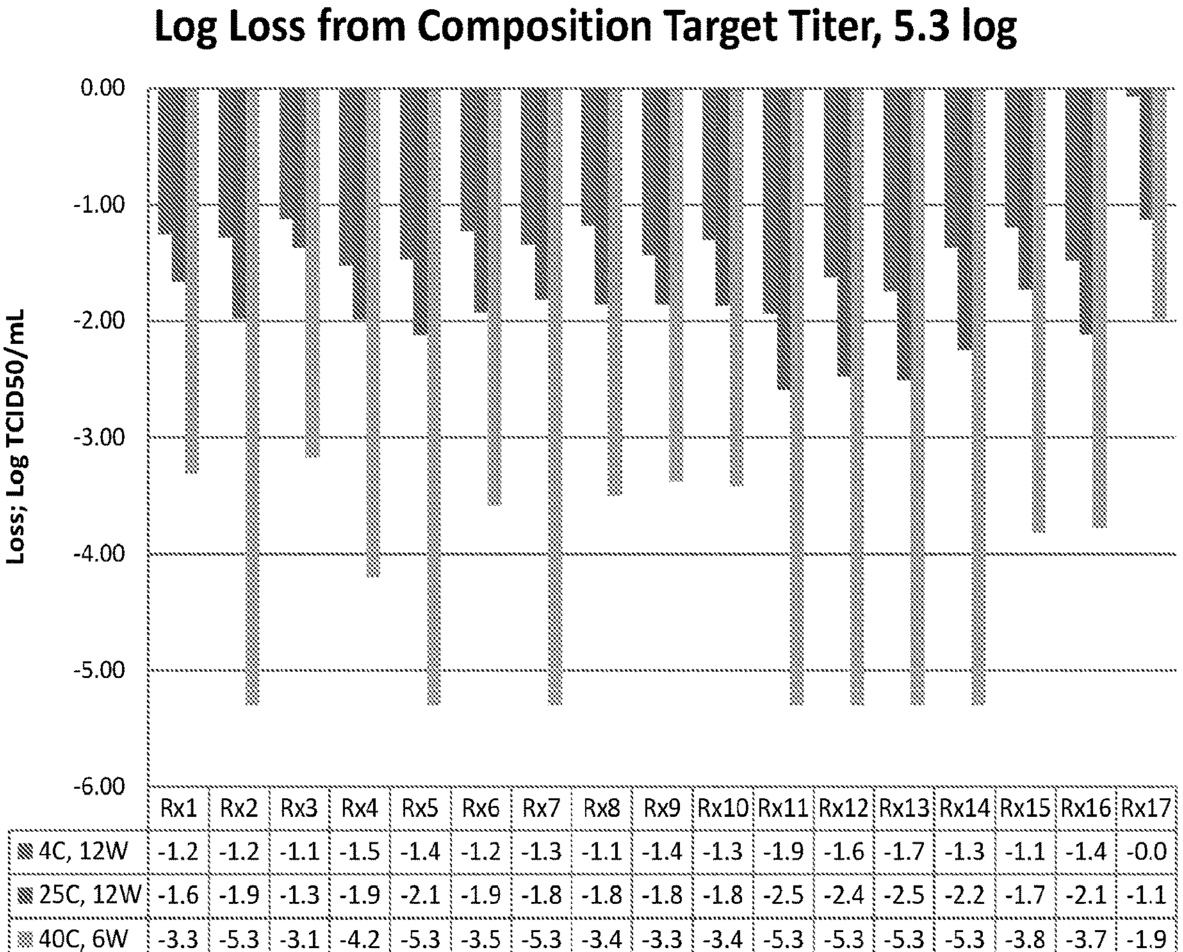
FIG. 13 is a histogram plot representing a cumulative overview of experiments using various compositions for testing stability of exemplary live, attenuated alphaviruses in one embodiment disclosed herein at various temperatures.

FIG. 13 is a histogram plot illustrating loss of titer during the above described stability studies. It was observed that all formulations maintained stable titers of live alphaviruses at least to week 12 at refrigeration temperatures of about 4° C. At room temperature, approximately 40° C., formulations 2, 5, 7, 11, 12, 13, and 14 exhibited significant loss by about 6 weeks. Formulations 1, 3, 9, 10, and 15 demonstrated enhanced stability compared with formulation 5 (equivalent to Formulation 6 in Example 1 above) for longer periods than 6 weeks at room temperature, about 40° C.

Figure 14:
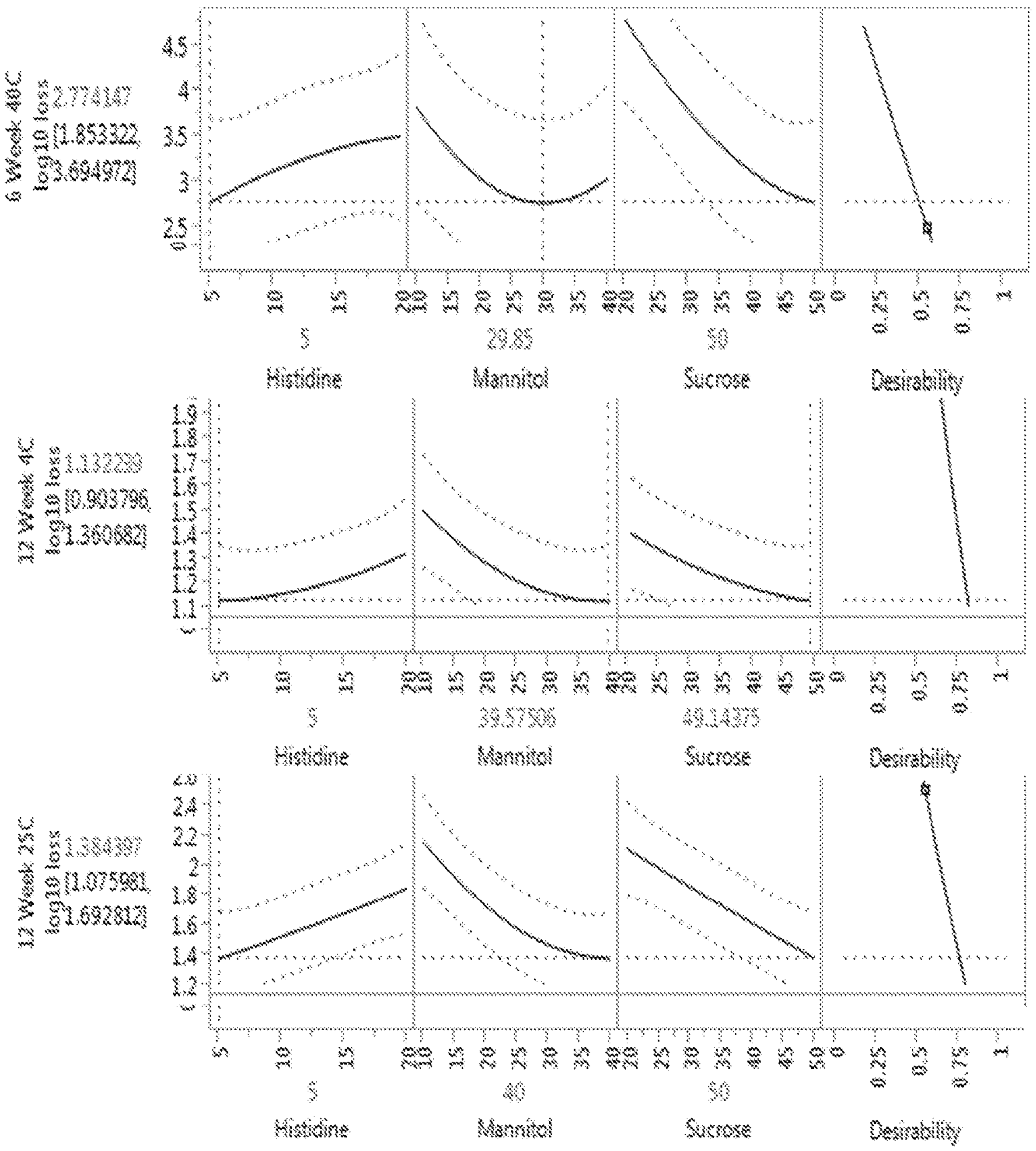
FIG. 14 are graphs of various agents under different conditions compared to the agent itself and other agents of use for predicting desirable stabilizing compositions for live, attenuated alphaviruses in one embodiment disclosed herein.
Figure 15:
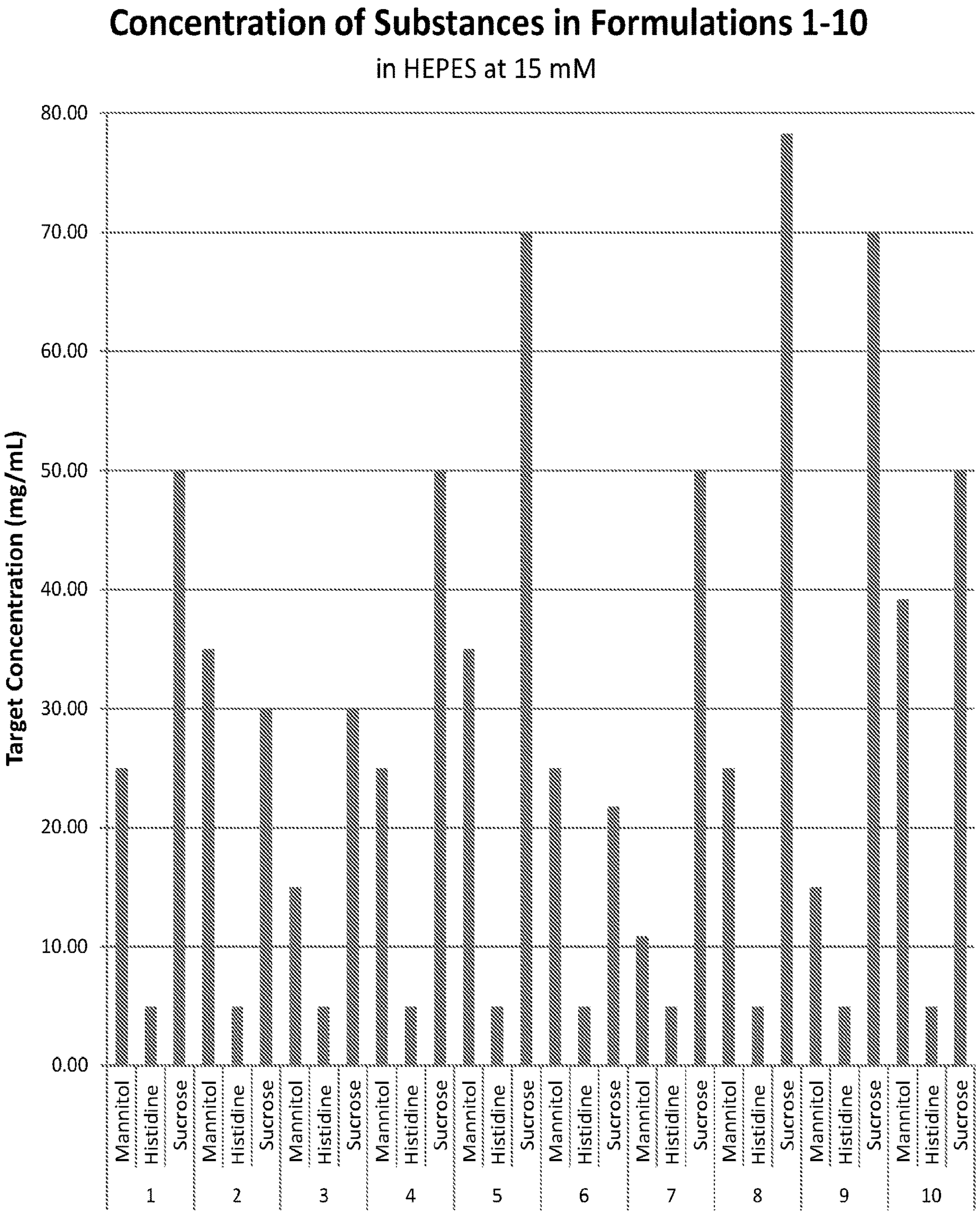
FIG. 15 is a histogram representing concentration ranges of various agents of use in one embodiment disclosed herein where the agents included in these exemplary compositions for stabilizing live alphaviruses are mannitol, histidine and sucrose.

FIG. 14 represents outputs that illustrate data from experiments using various formulations for predicting desirable traits in formulations for exemplary live alphaviruses. This data provides support that formulations having high concentrations of certain carbohydrate agents and low concentrations of certain amino acids exhibited an improved stability for several weeks at room temperature of about 40° C. Therefore, these specified formulations can be used in order to increase stability of live alphaviruses during transport, delivery and eventual administration to a subject. In addition, these exemplary formulations are without human or animal protein agents which can reduce adverse immune and other effects in a recipient.

Example 6

Stabilizing Formulations Absent Human or Animal Derived Protein Agents

In other exemplary methods, long term stability experiments at 40° C., 25° C., and 4° C. were performed to analyze effects of additional varying concentrations of carbohydrates (e.g. sucrose and mannitol) and amino acids (e.g., histidine) on live alphavirus stability, for example live, attenuated CHIK virus was used, based on observations that formulations having one or more carbohydrates and one or more amino acids had a positive effect on CHIK stability (see above). Using formulation VI presented above as a base formulation, formulations with varying concentrations of sucrose, mannitol, and histidine were formulated in a 15.0 mM HEPES buffer at pH 7.2+/−0.2. Further, the expansion of these target agents including compositions of mannitol, histidine, and sucrose were based on the observations in the 17 sample study above. Mannitol, sucrose, histidine, and HEPES were chosen in combination based on their performance in the 17 formulation study and for their non-animal origins. The target concentration chosen for mannitol and sucrose in this group of 10 formulations was based on statistical predictions using the data generated in previous experiments.

Exemplary Formulations:

1. 15.0 mM HEPES, 25.0 mg/ml Mannitol, 5.0 mg/ml Histidine, and 50.0 mg/ml Sucrose
2. 15.0 mM HEPES, 35.0 mg/ml Mannitol, 5.0 mg/ml Histidine, and 30.0 mg/ml Sucrose
3. 15.0 mM HEPES, 15.0 mg/ml Mannitol, 5.0 mg/ml Histidine, and 30.0 mg/ml Sucrose
4. 15.0 mM HEPES, 25 mg/ml Mannitol, 5.0 mg/ml Histidine, and 50.0 mg/ml Sucrose
5. 15.0 mM HEPES, 35.0 mg/ml Mannitol, 5.0 mg/ml Histidine, and 70.0 mg/ml Sucrose
6. 15.0 mM HEPES, 25.0 mg/ml Mannitol, 5.0 mg/ml Histidine, and 21.72 mg/ml Sucrose
7. 15.0 mM HEPES, 10.86 mg/ml Mannitol, 5.0 mg/ml Histidine, and 50.0 mg/ml Sucrose
8. 15.0 mM HEPES, 25.0 mg/ml Mannitol, 5.0 mg/ml Histidine, and 78.28 mg/ml Sucrose
9. 15.0 mM HEPES, 15.0 mg/ml Mannitol, 5.0 mg/ml Histidine, and 70.0 mg/ml Sucrose
10. 15.0 mM HEPES, 39.14 mg/ml Mannitol, 5.0 mg/ml Histidine, and 50.0 mg/ml Sucrose

TABLE 4

| Stability Designs | | | | | | |
|---|---|---|---|---|---|---|
| | weeks | | | | | |
| | 0 | 2 | 4 | 6 | 8 | 12 |
| 4° C. | x | x | x | | x | x |
| 25° C. | x | x | x | | x | x |
| 40° C. | x | x | x | x | | |

Example 7

Liquid and Lyophilized Formulations

Live, attenuated alphavirus samples formulated in these compositions were stored. In this study, live, attenuated chikungunya virus stability in various formulations based on the 17 sample study above were analyzed. Sample 17 in the above study was selected as the positive control. 15 samples per 10 formulations were stored at 4° C., 25° C., or 40° C. Samples formulations were studied for potency evaluation at the time points indicated in Table 4 and are exemplary results are illustrated in FIGS. 16-20. Samples incubated at 4° C. and 25° C. (FIGS. 19 and 18, respectively) were analyzed in parallel with samples incubated at and 40° C. (FIG. 17) to demonstrate the trend of titer remaining over 6-12 week periods.

Example 8

In another exemplary method, stability of lyophilized live, attenuated alphaviruses (e.g. CHIK) was evaluated. At week 0, all compositions 1-10 were analyzed for physiological features and exhibited cake appearance scores of higher than 3 and had residual moisture percentage <0.5% moisture (data not shown). The center point formulation (Rx 1 and 4 in this study) containing 25 mg/ml mannitol and 50 mg/mL sucrose met the positive physical criteria according to cake aesthetics (data not shown) while still achieving higher stability among formulations at both 25° C. and 40° C., critical temperatures for stability during transportation. In one example, these samples were duplicated in order to generate a more robust statistical data set around the excipient concentration center point of the experimental design.

Figure 16:
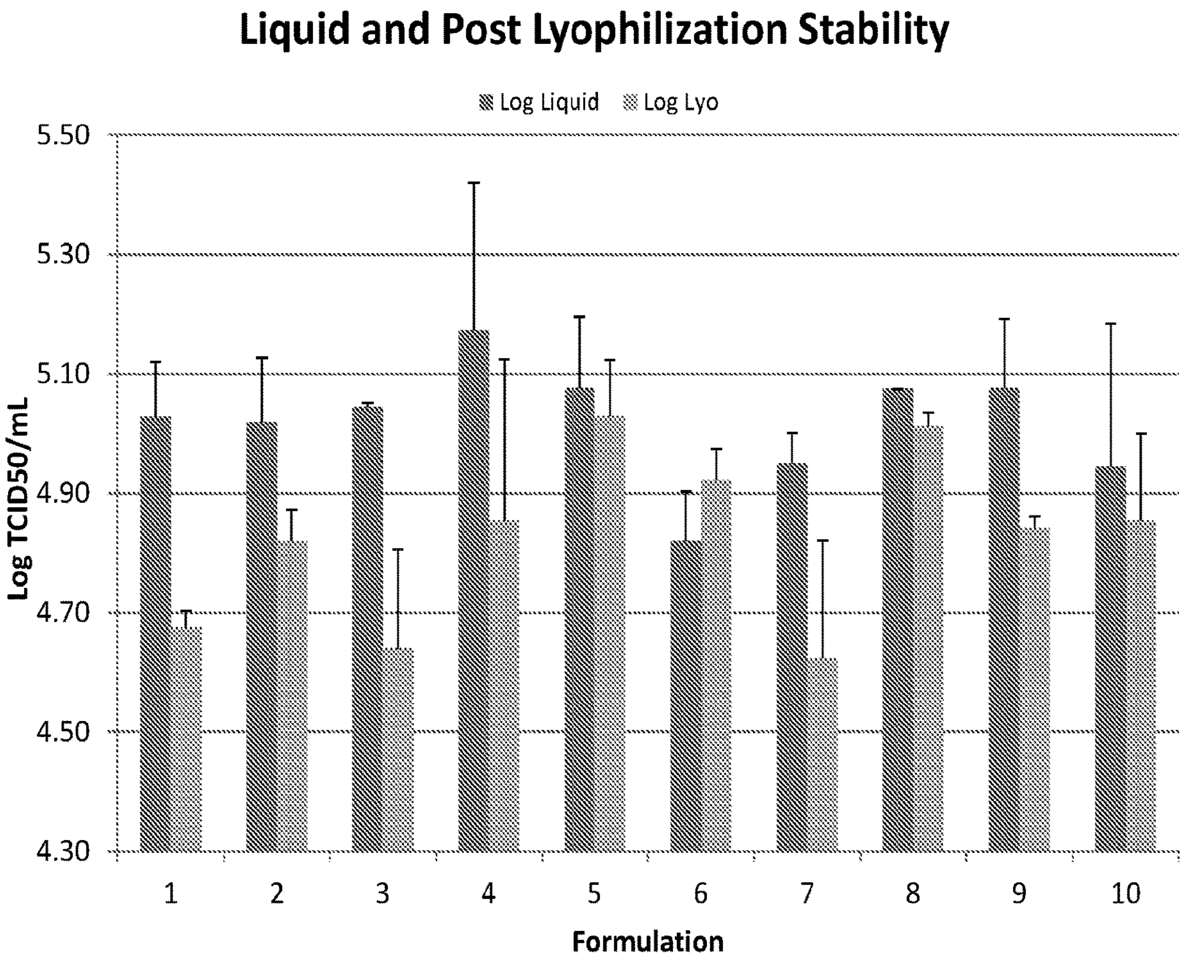
FIG. 16 is a histogram representing experiments using various compositions disclosed herein in liquid and lyophilized states for testing effects on live alphaviruses in one embodiment disclosed herein.
Figure 17:
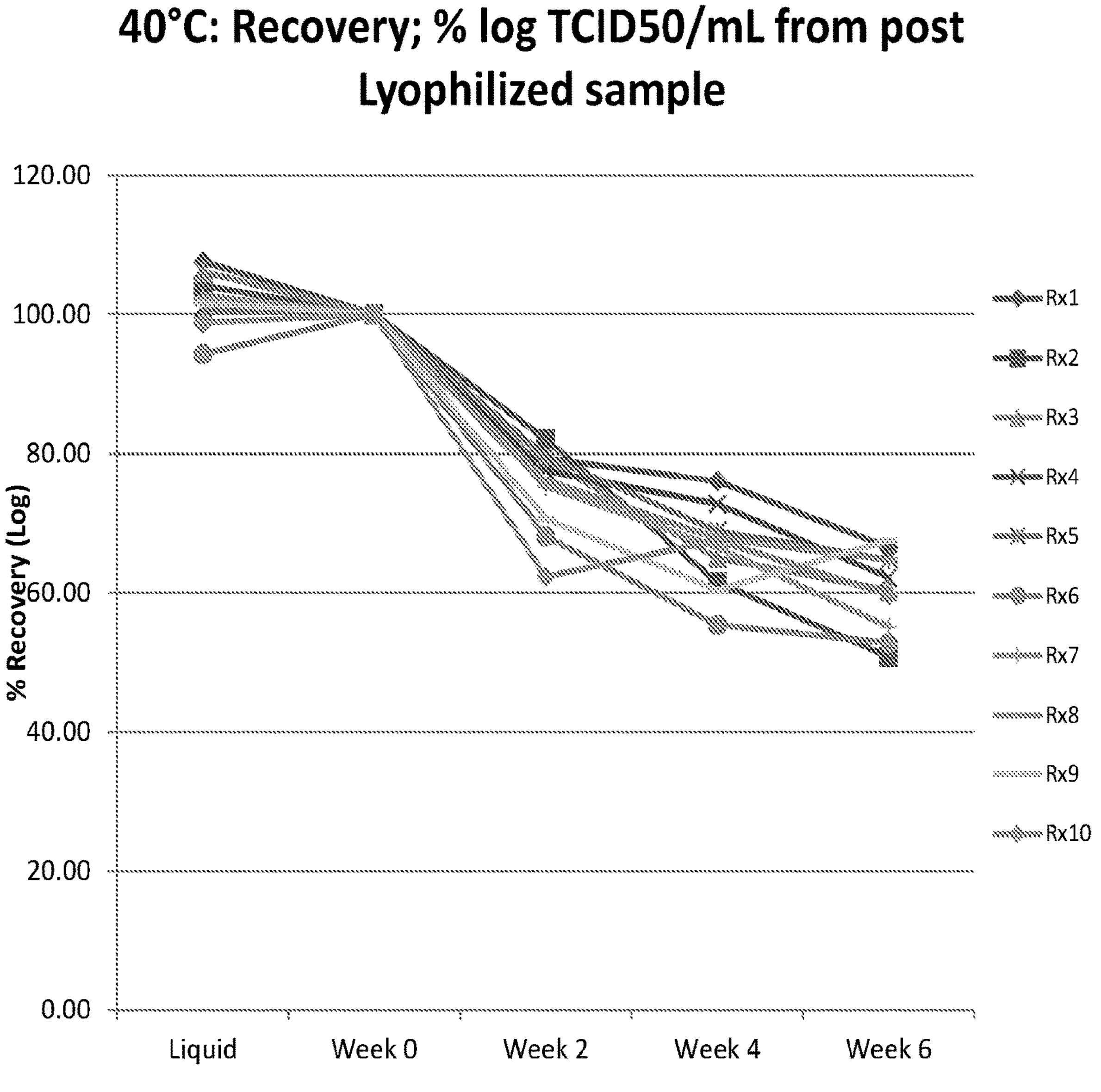
FIG. 17 is an exemplary graph representing experiments for testing stability of live alphaviruses in various formulations in one embodiment disclosed herein at about 40° C.

Some of these formulations exhibited higher remaining titers when lyophilized at week 0 (FIG. 16). For example, 1, 4, 5, 8 and 9 demonstrated higher titers in liquid form. While, formulas 5 and 8 demonstrated higher titers in lyophilized states (FIG. 16). Some of these formulations exhibited higher remaining titers upon freeze-thaw cycle (data not shown). In other experiments, lyophilized vaccine formulations 1-10 were stored at 40° C. (FIG. 17), 25° C. (FIG. 18), or 4° C. (FIG. 19) and assessed for overall titer loss at the various temperatures over the time period indicated. Samples taken at the indicated time points were reconstituted and titrated in Vero cells using indicators to calculate $TCID_{50}$. Exemplary live alphaviruses (e.g. live, attenuated CHIK virus) formulations 1, 3, 4, 5, 8, 9, and 10 of this test group were found to be stable for up to at least 6 weeks at 40° C. with >60% recovery while other formulations 2, 6, and 7 exhibited slightly reduced recovery at least to 6 weeks when stored at room temperature of about 40° C. (FIG. 17) when compared to formulations 1, 3, 4, 5, 8, 9, and 10. All tested formulas had at least 50% recovery at least 6 weeks after exposure to room temperature of about 40° C. for this time period. This is a significant improvement over other formulations in the art and tested herein.

Figure 18:
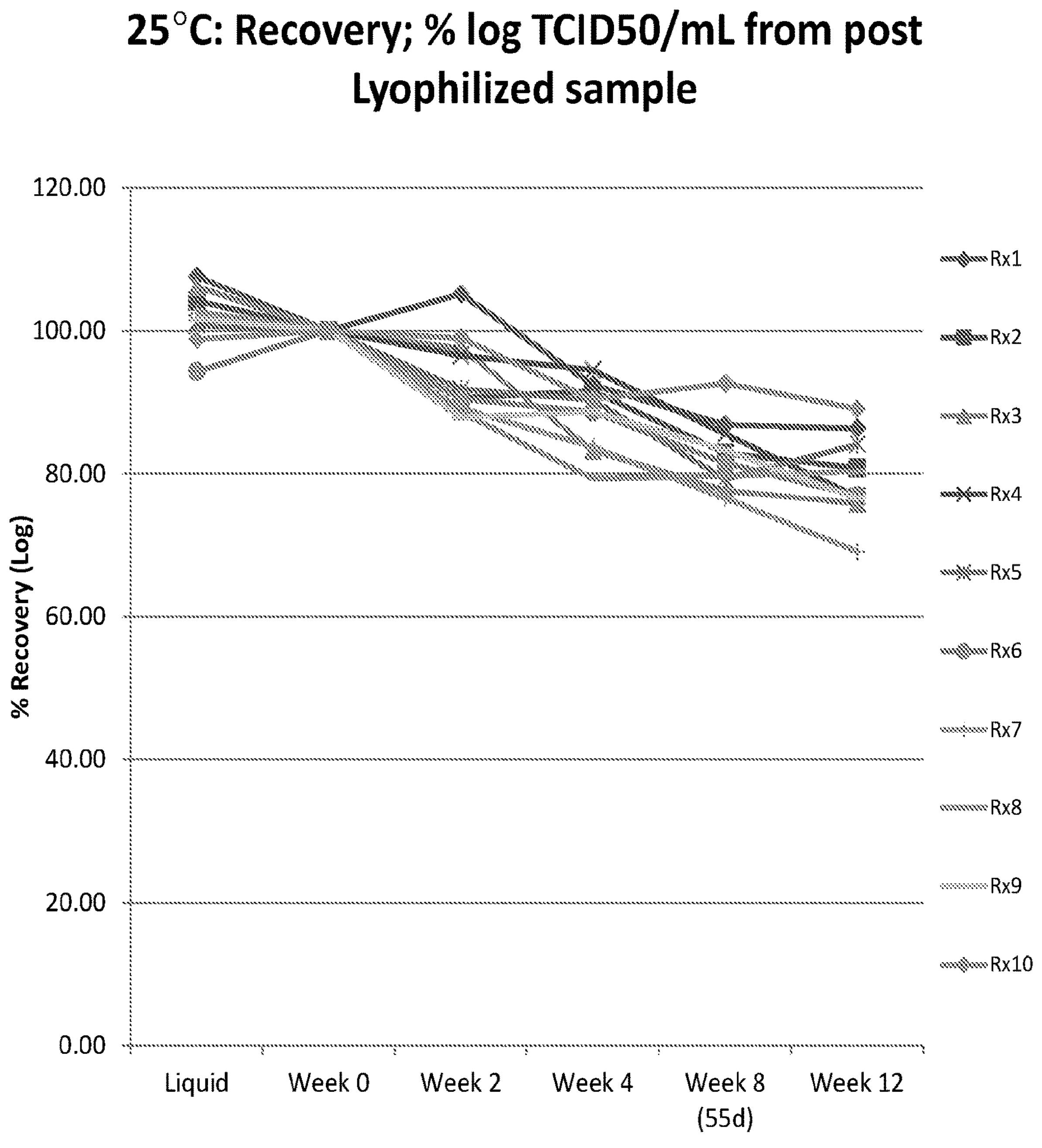
FIG. 18 is an exemplary graph representing experiments for testing stability of live alphaviruses in various formulations in one embodiment disclosed herein at about 25° C.
Figure 19:
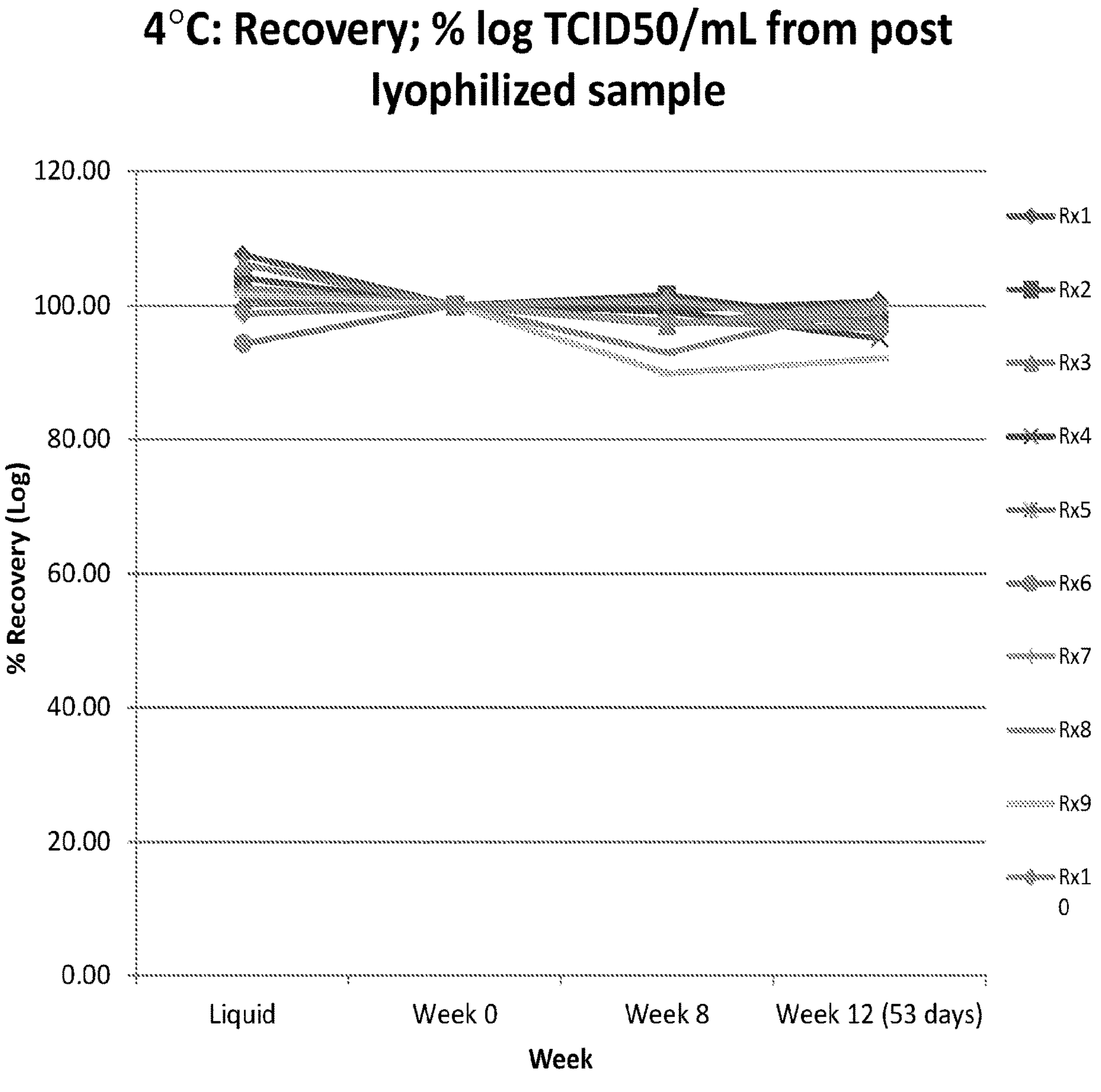
FIG. 19 is an exemplary graph representing experiments for testing stability of exemplary live alphaviruses in various formulations in one embodiment disclosed herein at about 4° C. or about refrigeration temperature.

Formulations 1, 2, 4, 5, 8, and 10 demonstrated at least 80% recovery for at least 12 weeks when stored at about 25° C. while formulations 3, 6, 7, 9 and 13 had slight titer loss when compared to the other tested formulations after about 8-12 weeks at 25° C. (FIG. 18). In spite of this comparible loss at 25° C., all formulations tested (1-10) demonstrated at least 70% recovery for at least 12 weeks when stored at about 25° C. (FIG. 18). All formulations tested (1-10) demonstrated only slight loss and had over 90% recovery when stored at refrigeration temperatures of about 4° C. for at least 12 weeks (FIG. 19).

Figure 20:
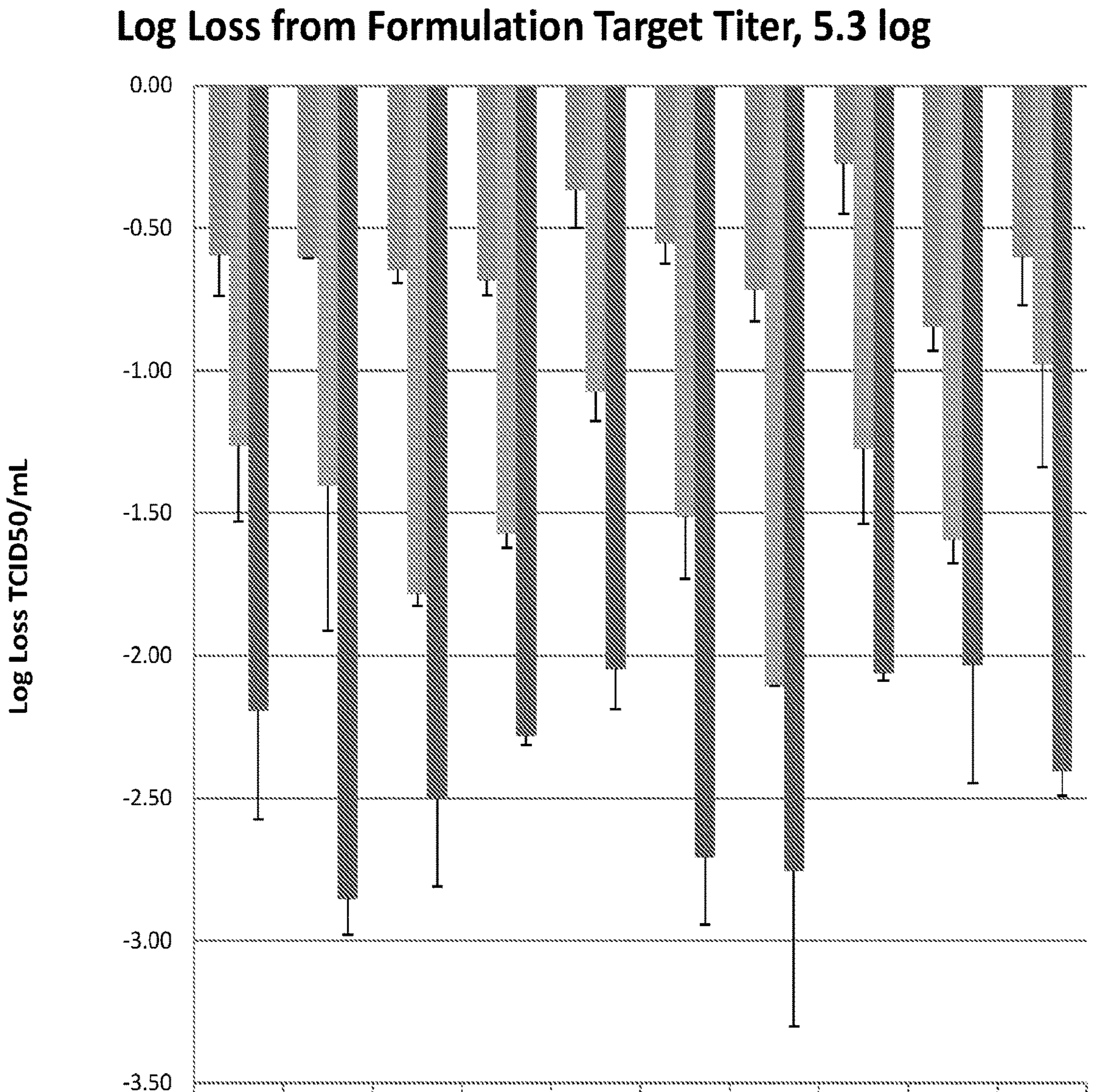
FIG. 20 is a histogram plot representing a cumulative overview of experiments using various compositions for testing stability of exemplary live, attenuated alphaviruses in one embodiment disclosed herein at various temperatures.

FIG. 20 is a histogram plot illustrating loss of titer during the above described stability studies. It was observed that all formulations maintained stable titers of live alphaviruses at least to week 12 at refrigeration temperatures of about 4° C. At room temperature, approximately 40° C., formulations 2, 3, 6 and 7 exhibited significant loss by about 6 weeks. Formulations 1, 8 and 9 demonstrated enhanced stability compared with formulation 2 for longer periods than 6 weeks at room temperature, about 40° C.

TABLE 5

| List of Abbreviation | |
|---|---|
| CHIKV | Chikungunya Virus |
| $TCID_{50}$ | 50% Tissue Culture Infective Dose |
| HB | Hepes Buffer Saline |
| HBS | Hepes Buffer Saline + Sucrose |
| HSG | Hepes Buffer Saline + Sucrose + Gelatin |
| IRES | Internal Ribosomal Entry Site |
| DMEM | Dulbecco's modified minimal essential medium |
| MCT | Microcentrifuge Tubes |
| PBS | Phosphate Buffered Saline |
| FBS | Fetal Bovine Serum |
| Pre-MVS | Pre-Master Virus Seed |

Materials and Methods

Individual aliquots of a predetermined dose of CHIK-IRES vaccine (pre-MVS, Mastervirus seed) were formulated in compositions containing buffers including HEPES buffered saline (HB), HEPES Buffered Saline containing sucrose (HBS), HEPES buffered saline containing sucrose and gelatin (HSG). Formulated hydrated or liquid vaccine was incubated at certain temperatures such as room temperature 25° C. and 40° C., and refrigeration temperature 4° C. Aliquots were removed from these formulations at predetermined intervals, and titrated for the presence of infectious alphavirus by $TCID_{50}$ in for example, 96 well plates with Vero cells.

Cell Lines and Tissue Culture

A research-grade Vero cell bank derived from the applicant's cGMP Working Cell Bank was prepared to perform these experiments. Vero cells were obtained: Vero (WHO) Working Cell Bank passage: 142 (lot # INV-VERO-WCB-001; $5 \times 10^6$), and were stored in liquid nitrogen. A vial was rapidly thawed in a water bath and directly inoculated into pre-warmed cDMEM (Dulbecco's modified minimal essential medium), about 19 milliliters containing penicillin-streptomycin, 40 mM L-glutamine and 10% FBS) in a T-75 $cm^2$ flask and incubated at 37° C., 5% $CO_2$. Cells were allowed to grow to confluency, and subcultured using PBS, Trypsin (HyClone, for example, cat # SH30042.01) and cDMEM-10. This flask was expanded to two T-185 $cm^2$ flasks and grown until the cells reached 100% confluency. Cells were harvested by trypsinization, centrifuged at 800×g for 10 minutes, and resuspended in DMEM containing 20% FBS and 10% DMSO at a concentration of $1\times10^7$ cells/mL.

Vero were grown and maintained in Dulbecco's modified minimal essential medium (DMEM) containing penicillin-streptomycin and 10% FBS (HyClone) (DMEM-10%-FBS). Trypsin was used to maintain cells. Two days before viral adsorption, 96-well plates were plated with $1.4\times10^5$ cells/mL in 100 uL per well of DMEM-FBS-10%. Incubators were monitored daily to maintain indicated temperatures. Virus dilutions, adsorption and TCID50 assays were performed in cDMEM-FBS 2%.

CHIK-IRES: Live, Attenuated Alphavirus

Molecular generation of a live, attenuated CHIK virus used in various methods described is designated CHIK-002 (previously described). CHIK-002 was generated by an IRES insertion and propagated in Vero cells. A pre-Master Virus seed stock was used for these experiments at a concentration of $10^5$ $TCID_{50}$/mL. Briefly, the CHIK pre-MVS was generated after infection of monolayers of Vero cells. CHIK-virus is secreted into the supernatant, and the virus is harvested from the medium after clarification/removal of the dead Vero cells. The CHIK-pre-MVS was stabilized in DMEM containing 10% FBS, and stored at −80° C.

Assay Method $TCID_{50}$ assay methods were used to quantify the amount of infectious virus present (potency or stability) in the virus-containing preparations. $TCID_{50}$ is defined as the level of dilution of a virus at which half of a series of replicates of infected wells in the 96-well plate shows signs of virus infectivity, as evidenced by for example, CPE (Cytopathic Effect). Vero cells were grown and maintained in Dulbecco's modified minimal essential medium (DMEM) containing penicillin-streptomycin, L-glutamine and 10% FBS (HyClone) (DMEM 10%-FBS). Aliquots of the formulated samples were rapidly thawed in a water bath and mixed. An initial dilution of pre-MVS into a working concentration was performed, and ten-fold dilution series of these samples were made in for example, cDMEM-2% FBS in 96-well plates. Diluted viruses were maintained at 4° C. prior to inoculation of the Vero cell monolayers. At the time of assay, the growth medium was aspirated from the 96-well plate, and 100 μL of each virus dilution was added to the wells. The plates were incubated for 3-5 days at 37° C. and 5% $CO_2$. Titer was calculated using the Spearman-Karber method.

Vaccine Formulations

Stability experiments were prepared with vaccines including research-grade vaccine preparations, and the CHIK-IRES pMVS derived internally. For screening of excipients and stability studies using various compositions provided herein, alphavirus formulations were prepared in a final volume of 500 μL containing $10^5$ $TCID_{50}$/mL virus per sample. Samples were prepared in bulk in indicated buffers/formulations and input samples were taken before the study was initiated as a measure of initial titer. Samples were aliquoted into MCT and stored for the indicated time and temperature. Each of the four formulations were prepared for 500 μL final with $10^5$ TCID50/mL virus per sample. 60 samples per formulation were prepared in bulk and input samples were taken before they were aliquoted into 1.5 mL MCT containing 500 uL.

Formulated Immunogenic Construct Storage

Immunogenic virus formulations were stored at 4° C. (Micro Climate Chamber; Model # MCB-12-33-33-H/AC) and at −80° C. (REVCO Elite Plus; Model # ULT2186-6-D43). Both systems were monitored with Dickson Wizard2—900 MHZ Logger (Model # WT-220 for 4° C. and WT-240 for −80° C.).

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A live attenuated alphavirus composition comprising:
one or more live alphaviruses;
one or more amino acids that include histidine;
two or more carbohydrate agents; and
wherein the composition does not include serum or gelatin and wherein the composition stabilizes live alphaviruses.

2. The alphavirus composition according to claim 1, further comprising HEPES buffer wherein the HEPES buffer concentration is 1.0 mM to 200.0 mM.

3. The alphavirus composition according to claim 1, wherein the one or more live alphaviruses comprise Chikungunya virus (CHIK), o'nyong'nyong virus, Ross River virus, Eastern equine encephalitis and Western equine encephalitis, other Semliki Forest virus, or other Togavirus and combinations thereof.

4. The alphavirus composition according to claim 1, wherein the one or more live alphaviruses are chikungunya (CHIK) viruses.

5. The alphavirus composition according to claim 1 wherein the live alphavirus comprises a live, attenuated alphavirus.

6. The alphavirus composition according to claim 1, wherein the composition is in aqueous form.

7. The alphavirus composition according to claim 1, wherein the composition is partially or wholly dehydrated.

8. The alphavirus composition according to claim 1, wherein the two or more carbohydrate agents are selected from the group consisting of one or more of trehalose, galactose, fructose, sucrose, chitosan, sorbitol, mannitol and a combination thereof.

9. The alphavirus composition according to claim 1, wherein the two or more carbohydrate agents comprise sucrose and mannitol.

10. The alphavirus composition according to claim 2, wherein concentration of the HEPES buffer concentration is from 10.0 mM to 150.0 mM.

11. The alphavirus composition according to claim 2, wherein the HEPES buffer concentration is from 10.0 mM to 30.0 mM; the two or more carbohydrate agent concentration is from 10.0 to 100.0 mg/ml; and the amino acid concentration is from 1.0 mg/ml to 20.0 mg/ml.

12. The alphavirus composition according to claim 2, wherein the HEPES buffer concentration is 15.0 mM; the two or more carbohydrate agent concentration is from 20.0 mg/ml to 70.0 mg/ml each; and the amino acid concentration is from 1.0 mg/ml to 10.0 mg/ml.

13. The alphavirus composition according to claim 2, wherein the alphavirus composition comprises HEPES buffer, histidine, sucrose, and mannitol.

14. The alphavirus composition according to claim 13, wherein the HEPES buffer concentration is 15.0 mM, histidine concentration is 1.0 mg/ml to 20.0 mg/ml; sucrose concentration is 20.0 mg/ml to 90.0 mg/ml; and mannitol concentration is 10.0 mg/ml to 50.0 mg/ml.

15. The alphavirus composition according to claim 13, wherein the HEPES buffer concentration is 15.0 mM, histidine concentration is 5.0 to 20.0 mg/ml; sucrose concentration is 40.0 to 90.0 mg/ml; and mannitol is 15.0 to 40.0 mg/ml.

16. The alphavirus composition according to claim 15, wherein the histidine concentration is 5.0 to 15.0 mg/ml; sucrose concentration is 40.0 to 80.0 mg/ml; and mannitol concentration is 15.0 to 40.0 mg/ml.

17. The alphavirus composition according to claim 1, further comprising a salt.

18. A live attenuated alphavirus composition comprising:
one or more live alphaviruses;
one or more salt agents;
one or more amino acids that include histidine; and
one or more carbohydrate agents that includes sucrose;
wherein the composition does not include serum or gelatin or other mammalian protein product and wherein the composition stabilizes live alphaviruses.

19. The alphavirus composition according to claim 18, further comprising HEPES buffer wherein the HEPES buffer concentration is 1.0 mM to 200.0 mM.

20. The alphavirus composition according to claim 18, wherein the one or more live alphaviruses comprise chikungunya virus (CHIK), o'nyong'nyong virus, Ross River virus, Eastern equine encephalitis and Western equine encephalitis, other Semliki Forest virus, or other Togavirus and combinations thereof.

21. The alphavirus composition according to claim 17, wherein the one or more live alphaviruses comprise live, attenuated alphaviruses.

22. The alphavirus composition according to claim 18, wherein the one or more live alphaviruses comprise live chikungunya virus (CHIKV).

23. The alphavirus composition according to claim 18, wherein the composition is in aqueous form.

24. The alphavirus composition according to claim 18, wherein the composition is partially or wholly dehydrated.

25. The alphavirus composition according to claim 18, further comprising at least one additional carbohydrate agent selected from the group consisting of: trehalose, galactose, fructose, chitosan, sorbitol, mannitol and a combination thereof.

26. The alphavirus composition according to claim 18, wherein the one or more salt agents are selected from the group consisting of: sodium chloride, monosodium glutamate (MSG), sodium phosphate, potassium phosphate, potassium chloride, and a combination thereof.

27. The alphavirus composition according to claim 19, wherein the HEPES concentration is from 1.0 mM to 40.0 mM.

28. The alphavirus composition according to claim 19, wherein the HEPES buffer concentration is from 1.0 to 30.0 mM; the one or more carbohydrate agents concentration is from 1.0% to 10.0%; and each of the one or more salt concentration is from 0.001% to 1.0% (w/v).

29. The alphavirus composition according to claim 18, wherein the composition comprises HEPES, sucrose, sodium chloride, monosodium glutamate, sodium phosphate, potassium phosphate, and potassium chloride.

30. The alphavirus composition of claim 29, wherein the HEPES buffer concentration is 15 mM, sucrose concentration is from 1.0% to 15.0% (w/v); sodium chloride concentration is 0.1% to 1.5% (w/v); monosodium glutamate concentration is from 0.05% to 0.5% (w/v); sodium phosphate concentration is from 0.01 to 0.15% (w/v); potassium phosphate concentration is from 0.01% to 0.1% (w/v); and potassium chloride concentration is from 0.01% to 0.1% (w/v).

31. A method for decreasing inactivation of a live alphaviruses comprising, combining one or more live alphaviruses with a composition comprising: two or more carbohydrate agents; and one or more amino acids that include histidine, wherein the composition decreases inactivation of the live alphavirus, and wherein the composition does not include serum or gelatin.

32. The method according to claim 31, further comprising HEPES buffer wherein the HEPES buffer concentration is 1.0 mM to 200.0 mM.

33. The method according to claim 31, wherein the live alphaviruses comprise chikungunya virus (CHIK), o'nyong'nyong virus, Ross River virus, other Semliki Forest virus complexes, Eastern equine encephalitis and Western equine encephalitis and combinations thereof.

34. The method according to claim 31, further comprising partially or wholly dehydrating the combination.

35. The method according to claim 31, further comprising partially or wholly re-hydrating the composition prior to administration.

36. The method according to claim 31, wherein the composition increases the shelf-life of an aqueous virus composition.

37. The method according to claim 31, wherein the HEPES buffer concentration is from 1.0 to 30.0 mM; the two or more carbohydrate agent concentration is from 1.0 to about 100.0 mg/ml each; and the amino acid concentration is from 1.0 to 40.0 mg/ml.

38. The method according to claim 32, wherein the composition comprises HEPES, histidine, sucrose, and mannitol.

39. The method of claim 38, wherein the HEPES buffer concentration is 15 mM, the histidine concentration is 5.0 mg/ml to 20.0 mg/ml; the sucrose concentration is 20.0 mg/ml to 90.0 mg/ml; and the mannitol concentration is 10.0 mg/ml to 40.0 mg/ml.

40. The method according to claim 31, further comprising a salt agent.

41. The method according to claim 31, wherein the live alphavirus composition is further formulated for use as a medicament for administration to a subject to reduce the onset of or prevent an alphavirus infection.

42. A method for decreasing inactivation of a live alphaviruses comprising, combining one or more live alphaviruses with a composition comprising: 0.1 mM to 200 mM HEPES buffer; one or more salt agents, one or more amino acids that include histidine; and two or more carbohydrate agents that includes sucrose, wherein the composition decreases inactivation of the live alphaviruses, and wherein the composition does not include serum or gelatin.

43. The method according to claim 42, wherein the live alphaviruses comprise chikungunya virus (CHIK), o'nyong'nyong virus, Ross River virus, other Semliki Forest virus complexes, Eastern equine encephalitis and Western equine encephalitis and combinations thereof.

44. The method according to claim 42, further comprising partially or wholly dehydrating the combination.

45. The method according to claim 42, further comprising partially or wholly re-hydrating the composition prior to administration.

46. The method according to claim 42, wherein the composition increases the shelf-life of an aqueous virus composition.

47. The method according to claim 42, wherein the two or more carbohydrate agents further comprise at least one of trehalose, galactose, fructose, chitosan, sorbitol, mannitol and a combination thereof.

48. The method according to claim 42, wherein the one or more salt agents comprises one or more of sodium chloride, monosodium glutamate, sodium phosphate, potassium phosphate, potassium chloride, and a combination thereof.

49. The method according to claim 42, wherein the HEPES buffer concentration is from 1.0 mM to 40.0 mM.

50. The method according to claim 42, wherein the HEPES buffer concentration is from 1.0 to 30.0 mM; the two or more carbohydrate agent concentration is from 1% to 10% each; and the salt agent concentration is from 0.001% to 0.2% (w/v).

51. The method according to claim 42, wherein the composition comprises HEPES, sucrose, sodium chloride, monosodium glutamate, sodium phosphate, potassium phosphate, and potassium chloride.

52. A kit for decreasing inactivation of a live alphaviruses comprising:

at least one container;

a composition comprising 0.1 mM to 40.0 mM HEPES buffer, two or more carbohydrate agents that include sucrose, and one or more amino acids that include histidine; and one or more live alphaviruses, and wherein the composition does not include serum or gelatin.

53. The kit according to claim 52, wherein the composition comprises HEPES, histidine, sucrose, and mannitol.

54. The kit according to claim 52, wherein the composition comprises a pharmaceutical composition comprising a pharmaceutically acceptable excipient.

55. A kit for decreasing inactivation of live alphaviruses comprising:

at least one container;

a composition comprising 0.1 to 40.0 mM HEPES buffer, one or more carbohydrate agents that includes sucrose, one or more salt agents that includes at least monosodium glutamate, one or more amino acids that include histidine, and live alphaviruses, and wherein the composition does not include serum or gelatin.

56. The kit of claim 55, wherein the composition comprises HEPES, sucrose, sodium chloride, monosodium glutamate, sodium phosphate, potassium phosphate, and potassium chloride.

57. The kit according to claim 52, wherein the live alphaviruses comprise live, attenuated alphaviruses.

58. The kit according to claim 53, wherein the live alphaviruses comprise chikungunya (CHIK) virus, o'nyong'nyong virus, Ross River virus, Semliki Forest virus complexes, Eastern equine encephalitis and Western equine encephalitis and combinations thereof.

59. A pharmaceutical composition according to claim 1, wherein the alphavirus composition is a live, attenuated alphavirus composition and further comprises a pharmaceutically acceptable excipient.

60. The pharmaceutical composition according to claim 59, for use in a method for protecting a subject from infections resulting from exposure to an alphavirus.

61. The pharmaceutical composition for the use as defined in claim 60, wherein the subject is a human, livestock or other domesticated animal.

62. A method for vaccinating a subject against an alphavirus infection resulting from exposure to an alphavirus, the method comprising:

providing a pharmaceutical composition according to claim 59, and administering an effective amount of the pharmaceutical composition to the subject.

* * * * *